United States Patent
Burgo et al.

(10) Patent No.: US 10,995,048 B2
(45) Date of Patent: May 4, 2021

(54) NATURAL 1,2-ALKANEDIOLS, COMPOSITIONS HAVING NATURAL 1,2-ALKANEDIOLS AND PROCESSES FOR MAKING THE SAME

(71) Applicant: Inolex Investment Corporation, Wilmington, DE (US)

(72) Inventors: Rocco V. Burgo, Mullica Hill, NJ (US); Michael E. Wright, Hurricane, UT (US); Gary B. Mosser, Tabernacle, NJ (US); Michael J. Fevola, Belle Mead, NJ (US)

(73) Assignee: INOLEX INVESTMENT CORPORATION, Wilmington, DE (US)

( * ) Notice: Subject to any disclaimer, the term of this patent is extended or adjusted under 35 U.S.C. 154(b) by 0 days.

(21) Appl. No.: 16/682,059

(22) Filed: Nov. 13, 2019

(65) Prior Publication Data
US 2020/0189995 A1  Jun. 18, 2020

Related U.S. Application Data

(63) Continuation of application No. 16/262,902, filed on Jan. 30, 2019.

(60) Provisional application No. 62/623,985, filed on Jan. 30, 2018.

(51) Int. Cl.

| | | |
|---|---|---|
| C07C 29/04 | (2006.01) | |
| C07C 31/20 | (2006.01) | |
| C07C 29/80 | (2006.01) | |
| B01J 23/06 | (2006.01) | |
| B01J 37/08 | (2006.01) | |
| B01J 21/04 | (2006.01) | |
| C11D 3/20 | (2006.01) | |
| C07C 1/24 | (2006.01) | |
| C07C 29/48 | (2006.01) | |
| C07C 11/02 | (2006.01) | |
| C07C 11/107 | (2006.01) | |
| C07B 41/02 | (2006.01) | |
| C07B 63/00 | (2006.01) | |
| A61L 2/18 | (2006.01) | |
| A01N 31/02 | (2006.01) | |
| A61K 8/34 | (2006.01) | |
| A61Q 5/00 | (2006.01) | |
| A61Q 11/00 | (2006.01) | |
| A61Q 19/00 | (2006.01) | |
| C11D 3/48 | (2006.01) | |

(52) U.S. Cl.
CPC .............. *C07C 29/04* (2013.01); *B01J 21/04* (2013.01); *B01J 23/06* (2013.01); *B01J 37/08* (2013.01); *C07C 1/24* (2013.01); *C07C 11/02* (2013.01); *C07C 11/107* (2013.01); *C07C 29/48* (2013.01); *C07C 29/80* (2013.01); *C07C 31/20* (2013.01); *C11D 3/2044* (2013.01); *A01N 31/02* (2013.01); *A61K 8/345* (2013.01); *A61L 2/18* (2013.01); *A61Q 5/00* (2013.01); *A61Q 11/00* (2013.01); *A61Q 19/00* (2013.01); *B01J 2523/27* (2013.01); *B01J 2523/31* (2013.01); *C07B 41/02* (2013.01); *C07B 63/00* (2013.01); *C07C 2521/04* (2013.01); *C11D 3/48* (2013.01)

(58) Field of Classification Search
None
See application file for complete search history.

(56) References Cited

U.S. PATENT DOCUMENTS

| | | | |
|---|---|---|---|
| 4,234,752 A † | 11/1980 | Wu | |
| 8,450,543 B2 † | 5/2013 | Peters | |
| 8,912,373 B2 † | 12/2014 | Wright | |
| 9,242,226 B2 † | 1/2016 | Wright | |
| 9,856,461 B2 | 1/2018 | Fortman | |
| 2003/0006523 A1 † | 4/2003 | Fuji | |
| 2005/0006538 A1 † | 3/2005 | De Bruyn | |
| 2006/0161025 A1 | 7/2006 | Osterholt | |
| 2012/0282207 A1 | 11/2012 | Lutz | |
| 2014/0066666 A1 | 3/2014 | Koch | |

FOREIGN PATENT DOCUMENTS

| | | |
|---|---|---|
| EP | 1876162 A1 | 1/2008 |
| WO | 2016007196 A1 | 1/2016 |

OTHER PUBLICATIONS

U.S. Appl. No. 16/262,902: Non-Final Office Action dated Sep. 17, 2020.
Liu et al., "Hydrogen peroxide-independent production of a-alkenes by OleTJE P450 fatty acid decarboxylase," Biotechnology for Biofuels 7:28 (2014).
Swern et al., "Hydroxylation and epoxidation of some 1-olefins with per-acids," JACS 68:1504-1507 (1946).

(Continued)

*Primary Examiner* — Nannette Holloman
(74) *Attorney, Agent, or Firm* — Cozen O'Connor

(57) ABSTRACT

A process is incorporated herein for the synthesis of bio-1, 2-alkanediols, comprising: providing a bio-alkene having a carbon chain of about 5 to about 20 carbon atoms and a bio-1-alkene regioselectivity of at least about 80%, at least about 92% and/or at least about 95%; and converting the bio-alkene to a bio-1,2-alkanediol having a carbon chain length of about 5 to about 20 carbon atoms. Methods for treating catalysts which may be incorporated in the process for the synthesis of bio-1,2-alkanediols are also included herein. Such bio-1,2-alkanediols are used in compositions and products alone as antimicrobial materials, or with existing bio-compounds and/or antimicrobials, preservatives, alternative preservation systems and/or hurdle technology components. The bio-1,2-alkanediols incorporate a natural and bio-based pathway for antimicrobial effects in various compositions such as cosmetic, pharmaceutical, industrial and household products.

28 Claims, 7 Drawing Sheets

(56) References Cited

OTHER PUBLICATIONS

Wang et al., Efficient conversion of microcrystalline cellulose to 1,2-alkanediols over supported Ni catalysts, Green Chem., 14:758-765 (2012).
Jong & Birmingham, Mushrooms as a Source of Natural Flavor and AromaCcompounds, Chapter 37 (pp. 345-366) in Mushroom Biology and Mushroom Products (Chinese University Press 1993).
Klug et al., Degradation of Hydrocarbons by Members of the Genus Candida, II. Oxidation of n-Alkanes and 1-Alkenes by Candida lipolytica, Journal of Bacteriology, vol. 93, No. 6, pp. 1847-1852 (1967).†

† cited by third party

NATURAL 1,2-ALKANEDIOLS, COMPOSITIONS HAVING NATURAL 1,2-ALKANEDIOLS AND PROCESSES FOR MAKING THE SAME

CROSS-REFERENCE TO RELATED APPLICATIONS

This U.S. Non-Provisional Patent Application is a continuation of co-pending U.S. patent application Ser. No. 16/262,902, entitled "Natural 1,2-Alkanediols, Compositions Having Natural 1,2-Alkanediols and Methods of Making Same", filed Jan. 30, 2019, which in turn claims the benefit under 35 U.S.C. § 119(e) of U.S. Provisional Patent Application No. 62/623,985, filed Jan. 30, 2018, entitled "Natural 1,2-Alkanediols, Compositions Having Natural 1,2-Alkanediols and Methods of Making Same," the entire disclosures of each if which are incorporated herein by reference.

BACKGROUND OF THE INVENTION

Field of the Invention

The invention herein relates to the field of natural and renewable, i.e., sustainable, antimicrobial components that enable alternative preservation systems for use in compositions applicable to various industries, including personal care, household and institutional or industrial cleaning products, medical or other related uses, and particularly in personal care compositions. More particularly to the preparation of natural and renewable 1,2-alkanediols, methods for making natural and renewable 1,2-alkanediols and compositions including such 1,2-alkanediols prepared from natural and renewable ("sustainable") feedstocks.

Description of Related Art

In most countries, including the United States, cosmetic and/or personal care ("personal care products") and other consumer products are manufactured and packaged in clean, but not typically sterile conditions, and many are sold in non-sterile forms. As a result, inconsequential (and usually harmless) amounts of bacteria, mold or yeast spores (collectively, "microbes") may be caught in products. In addition, once a consumer has purchased, opened and begun using such a product, further contamination may occur. For example, in personal care products, small amounts of microbes from the air or a consumer's skin may further contaminate the product.

Over time, during transit, storage or use the initial microbe population that was negligible may increase to a level significant enough to result in discoloration or fouling of the product, including the appearance of visible mold, which can impact the usefulness or performance of the product. In the case of personal care products or other consumer products that are applied or ingested (such as vitamins, etc.), it can have a health impact as well, and in some circumstances can lead to adverse skin reactions upon application, including infection.

To address the issue of microbial growth, manufacturers in the personal care industry and in other industries commonly add chemical preservatives, which are typically petrochemically based, to such products and compositions. However, the type and amount of preservative that can be used is subject to restrictions on several fronts: (1) legislative (in some countries, use of particular preservatives are prohibited); (2) technical (the type/amount of preservative must demonstrate its efficacy by meeting certain empirically assessed criteria ("challenge testing"); (3) consumer preference (consumers may perceive certain preservative chemicals as undesirable, such as petroleum-based or non-sustainable products, so products including them are not commercial viable); (4) logistical (e.g., the selected preservative must be effective in the relevant chemical environment (where parameters such as pH, hydrophobicity/hydrophilicity, etc. may vary) and production-cost friendly); and (5) sustainability, i.e., it should be prepared using sustainable processes and feedstock sourcing as described further herein.

There is also a desire to develop alternatives to traditional preservation and to find more user-friendly chemical component combinations that are derived from sustainable and renewable resources (i.e., "feedstocks"). These natural and renewable antimicrobial components and alternatives to traditional preservatives ("alternative preservation"), should provide equal or better protection and performance to the consumer.

To resolve issues with traditional preservatives, the applicant herein developed a prior art preservative for personal care compositions that does not include parabens, formaldehyde donors or chlorinated compounds, that can be used in all types of personal care formulations (e.g., both "leave-on" and "rinse-off" products). Such paraben-free or other non-petroleum-based alternative preservation products are attractive to consumers. The paraben-free preservative demonstrates efficacy against a broad spectrum of microorganisms at various levels of pH, especially around neutral pH levels which hare typically in or on the human body. This preservative is described in U.S. Patent Publication No. 2017/0360035 A1, in which one of the components in that preservative system is a 1,2-alkanediol.

Another attempt in the art to reduce the use of traditional preservatives is in the application of "hurdle technology." Hurdle technology is the practice of applying several types of restricting or preservative materials or processes so that microbes have a "hurdle(s)" to overcome before they can proliferate to spoilage levels (e.g., adding something to change pH to reduce proliferation and a smaller amount of preservative or other compound that together retard or create "hurdles" to microbial growth). Use of alternative preservation can be one step or "hurdle" in hurdle technology.

There is a need in the art to further develop "alternative preservation" additives. These alternative preservation systems include consumer-friendly, paraben-free materials that move away from traditional preservation or antimicrobials and towards "natural" and "sustainable" ("renewable") formulations and feedstocks, as those terms are defined hereinbelow.

One diol employed in preservation, caprylyl glycol, is believed by the applicant to be the fastest growing alternative preservation component in the world. Other 1,2-alkanediols such as 1,2-hexanediol, 1,2-decanediol, and 1,2-dodecanediol are also growing in popularity and function in alternative preservation formulations.

An example of one reaction sequence to prepare caprylyl glycol (1,2-octanediol) using an alkene as a key starting material is shown below. The starting material used is a petrochemically-derived 1-octene:

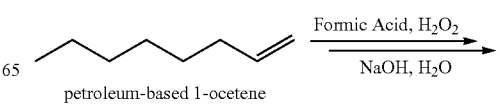
petroleum-based 1-ocetene

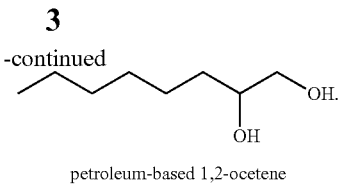

petroleum-based 1,2-ocetene

In the above reaction sequence, a petrochemically-derived 1-octene is reacted in the presence of formic acid and peroxide to form an intermediate chemical mixture which, e.g., undergoes a further ring-opening reaction in water with sodium hydroxide to complete formation of the 1,2-octanediol. This provides an excellent alternative preservation additive and is paraben-free, however, the starting material (i.e., 1-octene) is derived from a fossil-based (petrochemical) resource and importantly, represents a non-renewable feedstock, i.e., a non-sustainable resource.

Thus, as noted above there is a need for more consumer- and eco-friendly, alternative preservation systems (used alone or as part of hurdle technologies), including those that are paraben-free. There is further a need in the art for a material that is an alternative preservation material or that may be used in an alternative preservation system that is a 100% natural and renewable ("sustainable") feedstock to create an antimicrobial agent that can be used as or in alternative preservation systems. An example of a "natural" antimicrobial is one that is prepared from a bio-derived feedstock (e.g., from current and sustainable agricultural activities, like non-GMO based-fermentation, algae-, plant- or vegetable-derived, e.g., it comes from vegetable sources, or biomass, and it is not petrochemically-derived (such as being derived from sustainable tree and plant farms active in the 21$^{st}$ century). Such feedstocks are referred to herein as "natural" and "renewable" (i.e., "sustainable") and are known as a non-petroleum-derived feedstock. Further, such materials are formed by "new" carbon and not from petroleum or other fossil fuel sources ("old" carbon). Such products are referred to herein as "natural" products and are known in the art as non-petrochemically-derived or "bio" products. By "sustainable," herein, the applicants are referring to materials that come from renewable sources, and not those that deplete a limited natural resource, such as a fossil fuel or other non-renewable resource such as petroleum. Thus a natural or bio product, which is not petrochemically derived, and/or is made from sources that are not petrochemically derived would be sustainable and renewable.

True natural products (bio-compounds) are formed using biomass (e.g., material stored from carbon cycle processes in living plants and roots, etc. or released through animal respiration or through decomposition). When carbon decomposes and is broken down over millions of years under pressure, it creates fossil fuels (the source of petrochemically-derived carbon). Bio-compounds herein are intended to include materials derived from the carbon of plant sources/biomass, that exist recently and are also sustainable, and are not derived from fossil fuels.

These bio-based or "natural" feedstocks may be used in the production of alternative preservation formulations. The bio-based or "natural" products from such feedstocks may be tested to determine that they come from a true, natural and sustainable (as those terms are defined herein) feedstock source. Some products are known or advertised as being from natural sources when, in fact, they may not be prepared from truly natural and/or sustainable feedstock. A natural organic product is typically defined as a compound produced naturally by a living organism. To distinguish a petroleum-based product from a truly natural and/or sustainable product, one must test for the authenticity using established and credible test methods. The most current method employs a detailed analysis of stable isotopes using mass spectroscopy and evaluating carbon-12/carbon-13 and/or hydrogen-1/hydrogen-2 ratios. Such testing is available through several analytical service testing organizations and is much faster, more cost effective, and yields more detailed information compared to radiocarbon testing methods.

Stable isotope analysis is based on the principle of kinetic isotope effect. The latter effect is well-known to those in the art of chemical kinetics. In the broadest terms, heavy isotopes of a particular element react slower than their lighter equivalent (e.g., carbon-12 as opposed to carbon-13). So, as plants incorporate carbon dioxide into their biomass, the ratio of carbon-12 to carbon-13 will vary depending on the type of chemistry used in the plant to make biomass (e.g., whether the plant undergoes a $C_3$ or $C_4$ photosynthesis pathway). This is commonly reported as the $\delta^{13}C/^{12}C$ ratio (i.e., $\delta^{13}C$), and is referenced to a current carbon dioxide standard. In addition, similar isotope kinetic effects are observed when water is incorporated into new biomass, and this is measured as the $\delta^2H/^1H$ ratio (i.e., $\delta^2H$). Using a combination of $\delta^{13}C$ and $\delta^2H$ ratios, one familiar with in the relevant art is able to readily distinguish and validate the nature of the feedstock that was used to prepare the product being analyzed (i.e., whether it is petrochemically-derived or derived from recently living or living algae-, plant- or similar bio-sources).

In FIG. 2, it can be seen in general terms how isotope ratios can be used to determine the source of various detergents that have a strong relation to the feedstocks described herein, like 1-octanol. From the plot in FIG. 2, the $\delta^2H$ values have a more clearly defined difference between petroleum-based and renewable feedstocks and so in this case prove more valuable and defining than the $\delta^{13}C$ values. However, the combination using $\delta^2H$ and $\delta^{13}C$ values together is a preferred technique employed in the invention herein to prove a feedstock is, in fact, natural and renewable.

Radiocarbon is an unstable isotope of carbon, known as $^{14}C$. $^{14}C$ is an unstable isotope that emits radiation energy in the form of beta particles at a very consistent rate and ultimately decays to the more stable $^{14}N$ (i.e., a half-life for radiocarbon is 5730 years). Because petroleum-based (i.e., petrochemically-derived) feedstocks are derived from plants and animals buried millions of years ago, the feedstocks' radiocarbon (i.e., $^{14}C$) has been lost to decay. The ASTM International standards provide testing standards to determine the authenticity of a "bio-based compound" using radiocarbon, which may be found in ASTM D6866-16. This standard distinguishes newer carbon from carbon derived from fossil-fuel, or petroleum- and petrochemically-derived sources, i.e., "old carbon." The amount of $^{14}C$ in recent or current biomass is known, so a percentage of carbon from a renewable source can be estimated from a total organic carbon analysis, which provides the data necessary to determine if a compound is truly derived from a "natural" and/or "sustainable" ("renewable") feedstock source or is derived conversely from a compound of "old" sequestration (i.e., a petrochemically-derived or petroleum-based source). The use of petroleum-based or often labeled fossil-based feedstocks is generally accepted as being non-sustainable, i.e., old carbon is a non-sustainable and not a renewable feedstock, and furthermore, is not considered "natural" and "sustainable" in the art. As defined herein, it would not be considered to be a "natural" product or useful in a "natural" formulation. Hence, use of such feedstocks does not represent a path forward to development of "natural" and "renewable" alternative preservatives.

Dehydration of terminal alcohols using traditional methods to form alkene starting materials chemically yields a mixture of 1-alkenes, 2-alkenes, and 3-alkenes due to rearrangements and migrations of the 1-alkene product during the dehydration process. Using such a mixture of alkenes ultimately provides a mixture of diols upon dihydroxylation, providing a low yield of the desired terminal 1,2-diol material and unwanted contaminants.

In one known path of forming caprylyl glycol (1,2-octanediol) starting with 1-octanol, made from petrochemically-derived (i.e., petroleum-derived or fossil fuel-derived) feedstocks, the following reaction is known to occur:

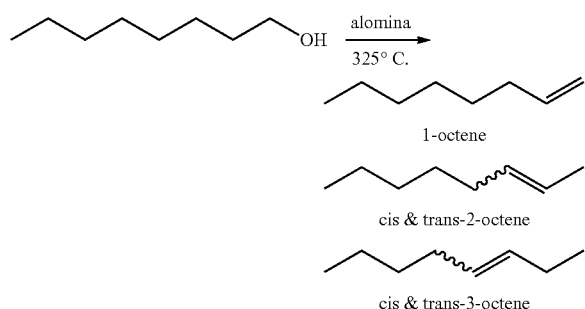

TABLE A

| Catalyst | 1-Octene (%) | 2-Octene & 3-Octenes (%) | 1-Octanol (%) | 1-Octene Selectivity (%) |
|---|---|---|---|---|
| Alumina | 87.7 | 5.3 | 4.7 | 94.3 |

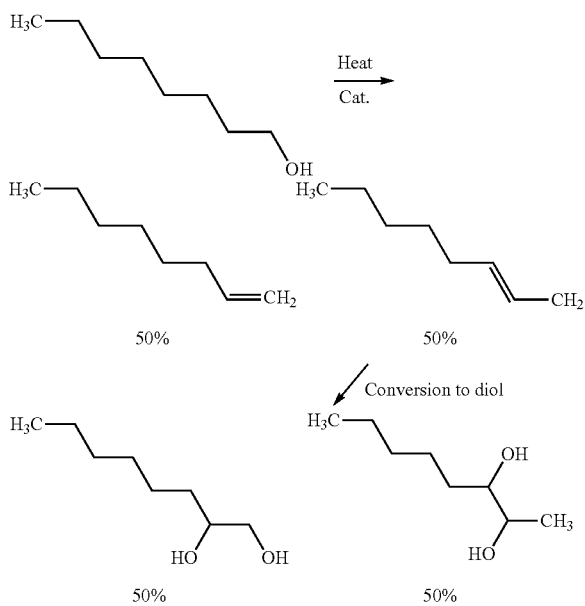

As can be seen from the above-reaction schemes, the use of heat and a traditional acid catalyst converts 1-octanol to an alkene, i.e., octene. Exposure to the acid sites in the catalyst allows the more thermodynamically stable 2-octene to form along with 1-octene. The 2-octene regioisomers formed (including 3-octene as shown above and 4-octene (not shown)) are very difficult to separate from the 1-octene and afford a lower net chemical yield of the desired 1-octene. It follows that an increased or higher regioselectivity is a critical factor in the catalytic dehydration of 1-octanol to 1-octene and a desired goal to achieve in the relevant art. When using renewable and natural feedstocks, reaction efficiency (i.e., chemical yield) of the desired product (i.e., 1-alkenes) is critical. There remains a need in the art for a highly regioselective dehydration of 1-octanol that also has high chemical conversion using efficient process equipment and operating in a rapid and energy efficient manner.

Thus, traditional pathways using an octene mixture of regioisomers as shown above for conversion to a desired terminal 1,2-octanediol is reduced and the yield is also reduced. This makes the ability to form the desired alternative preservative materials chemically inefficient and not cost effective, creates more waste in process, and makes the overall process less sustainable. There is a strong need in the art for a highly regioselective, and high-chemical conversion rate process for creating a bio-1-octene from a bio-1-octanol.

International patent Publication No. WO 2004/078336 A2 uses a γ-alumina having no additional promoters but that was instead given a very large pore size and volume to enhance regioselectivity for dehydration of 1-octanol. In this work, the regioselectivity was high (97.7%), but, the chemical conversion was 65% and product selectivity for octenes was only 25%. Thus, the chemical yield of 1-octene from 1-octanol using this catalyst system was only about 15.9%.

In another example, U.S. Pat. No. 7,576,250 B2, formation of 1-octene by cracking an ether derivative of 1-octanol is described. In this patent, the 1-octanol must first be converted to the methyl ether (i.e. methyl octyl ether) and then the ether is subjected to and passed over a γ-alumina catalyst. This involves extra chemical and added cost to make the ether and loss of the methanol in the process leading to a very ineffective and atom inefficient method. Most notably, the catalyst goes from having good conversion and regioselectivity in the first few hours, then, in just a mere 20 h of time-on-stream ("TOS"), all catalysts disclosed in the art show a constant and significant decrease in chemical conversion with a concomitant loss in regioselectivity. This type of short catalyst life time is not acceptable in commercial production efforts.

A lead-containing alumina catalyst is described in Chinese Patent No. 105312044 B, wherein plumbite pseudo-boehmite showed high apparent selectivity and conversion. The catalyst had a carbon deposition rate of ~0.04%/h, which is highly undesirable and would be unsatisfactory for something like 1000 h of continuous operation. Even more limiting is these catalysts incorporate a toxic heavy metal, namely lead. The use of these catalysts would require costly environmental controls and worker safety precautions if used on the industrial scale for commercial production One path to making a "natural" alkanediol is by fermentation of biomass to form a straight chain, linear alkanediol. For example, U.S. Patent Application Publication No. 2005/0069997 A1 teaches formation of 1,3 propanediol from fermentation broth. However, 1,3-propanediol is not a 1,2-alkanediol. Fermentation processes that form long chain diols are chemically inefficient (i.e., poor life-cycle-analysis numbers) and additionally require use of GMO-bacteria or -yeast, especially if one attempts to make a long carbon 1,2-alkandiol.

Another example of a natural bio-alcohol that is described in the art is bio-1-butanol, a known substance that has been used in commercial production since the discovery by Pasteur in 1862 of the acetone-butanol-ethanol fermentation process carried out by *clostridum* bacteria (a non-GMO bacteria), although it is used in very limited quantities currently. These bacteria ferment both $C_5$ and $C_6$ sugars to form a mixture of acetone, 1-butanol and ethanol (i.e., ABE). Since the discovery of ABE, advances in fermentation processes can provide optimized production of bio-1-butanol over acetone and ethanol production. While the production is improved, it remains difficult and energy intensive to purify the bio-1-butanol from the fermentation broth and other impurities involved in the fermentation process such as ethanol and acetone. In addition, applicant is unaware of a non-GMO bacteria or yeast process that can form longer chain alcohols (i.e., chains of six or more such as 1-hexanol or 1-octanol).

Bio-1-butanol is known as a source to make biofuels and provides a pathway for converting straight-chain, linear, primary four-carbon alcohols to bio-1-alkenes at very high yield to improve biofuel production and can also be used, for example in production of eco-friendly tires. In this method, bio-1-alcohols are dehydrated to bio-1-alkenes with high selectivity and chemical yield. The resulting bio-1-alkenes are useful in preparing high flashpoint diesel and jet biofuels useful for civilian and military applications. The bio-1-butanol is dehydrated using a solid phase dehydration catalyst that includes an inorganic support, such as γ-alumina or zinc aluminate ($ZnAl_2O_4$), and that has been treated/modified with a basic aqueous solution. The support may be further treated with an organosilane diluted in at least one hydrocarbon solvent. The process can convert bio-1-butanol from a fermentation process that contains 0.1 to about 90 wt % water and produces a corresponding 1-alkene at a 92-99% regioselectivity, with only a single pass over the solid-phase catalyst, produing a reaction conversion of greater than 95% and a chemical yield of greater than 90% of the bio-1-butene. However, even with such a result for bio-1-butene, it is noted that the conversion of 1-octanol to 1-octene is not simply a homolog of a conversion of 1-butanol to bio-1-butene. In fact, comparative examples described herein below, illustrated that silanization of the catalyst leads to a loss of regioselectivity for the dehydration chemistry of 1-octanol.

Based on the foregoing, while progress has been made, there is a need in the art for continued improvement to consumer products such as personal care products, household products, industrial products and pharmaceutical products to provide additives, especially for antimicrobial use or for boosting the effects of known preservatives or alternative preservation systems, so as to keep products safe from contamination and fresh in storage and in use, while avoiding traditional preservatives and finding and relying on components for consumer product compositions from natural bio-sources. There is more particularly a need for a natural, and preferably renewable/sustainable feedstock source to create a natural, bio-caprylyl glycol (i.e., a natural or bio-1,2-octanediol) and the associated bio-1-alkene intermediate.

BRIEF SUMMARY OF THE INVENTION

The invention provides efficient pathways to achieve a 100% "natural" or "bio-compound" that is an authentic "natural" material, and preferably includes bio-1,2-alkanediols of carbon lengths from about 5 to about 20, and preferably from 5 to about 14, that can be used alone, in combinations of different types of bio-1,2-alkanediols, or in blends with other natural or traditional antimicrobials and other cosmetic additives.

The invention includes a process for the synthesis of bio-1,2-alkanediols, comprising: providing a bio-alkene having a carbon chain of about 5 to about 20 carbon atoms and a bio-1-alkene regioselectivity of at least about 80%; and converting the bio-alkene to a bio-1,2-alkanediol having a carbon chain length of about 5 to about 20 carbon atoms.

In one embodiment of the process, the bio-alkene and the bio-1,2-alkanediol each have a carbon chain of about 6 to about 14 carbon atoms. The bio-alkene and the bio-1,2-alkanediol each may have a carbon chain length of about 6 to about 10 carbon atoms. The bio-alkene and the bio-1,2-alkanediol each may have a carbon chain length of about 6 to about 8 carbon atoms. For example, the bio-alkene may be bio-octene and the bio-1,2-alkane diol may be bio-1,2-octanediol.

In a further embodiment of the process, the bio-alkene preferably results from a process wherein a bio-1-alcohol is dehydrated by heating the bio-1-alcohol in a reactor with a catalyst. The reactor may be a fixed bed reactor. The fixed bed reactor may also be, e.g., a fluidized fixed bed reactor. In such an embodiment, the catalyst may be selected from $ZnAl_2O_4$ and a γ-alumina catalyst.

The bio-alkene in a preferred embodiment has a bio-1-alkene regioselectivity of about 92% to about 99%, and preferably about 95% to about 99%. The process also preferably yields at least about 92% to about 99% of the bio-1,2-alkanediol.

As noted above in one embodiment a catalyst treatment may be used. The catalyst may be a γ-alumina catalyst treated with a base to form a modified γ-alumina catalyst. The base may comprise a Group I or a Group II metal. The γ-alumina catalyst may be treated, e.g., with a calcium promoter to provide a modified γ-alumina catalyst. The modified γ-alumina catalyst may then be calcined to provide a calcined γ-alumina catalyst. In one embodiment, wherein a calcium promoter is used, the calcium promoter may be used in an amount of about 0.01 weight percent to about 4 weight percent based on the weight of CaO determined after calcination, and preferably about 1 weight percent to about 2 weight percent based on the weight of CaO determined after calcination.

A preferred temperature during calcination is about 400° C. to about 500° C., more preferably about 420° C. to about 480° C., and most preferably about 440° C. to about 460° C. Calcination may be carried out in an oven. The calcination may be performed in air or under an atmosphere of nitrogen or other inert gas(es).

The bio-alkene preferably undergoes a distillation step to refine the bio-alkene prior to converting the bio-alkene to the bio-1,2-alkanediol. The bio-1,2-alkanediol formed from the bio-alkene may also undergo a final distillation step to refine the bio-1,2-alkanediol.

In another embodiment of the process, the bio-alkene may result from a process wherein the bio-1-alcohol in water is dehydrated by heating the bio-1-alcohol with a catalyst using no purge gas or under a purge gas. The purge gas may preferably be nitrogen but other inert gases may be used within the scope of the invention.

The bio-alkene in the process may also be converted to the bio-1,2-alkanediol by reacting the bio-alkene in the presence of at least one of peracid, e.g., formic acid or acetic acid, and hydrogen peroxide to form a mixture of bio-1,2-epoxyalkane having an epoxy ring and bio-1,2-alkanediol, and contacting this mixture with water and sodium hydroxide to complete formation to the bio-1,2-alkanediol.

The overall process preferably process yields at least about 60% to about 99% of the bio-1,2-alkanediol, and more preferably yields at least about 72% to about 99% of the bio-1,2-alkanediol.

The invention further includes a process for making bio-1,2-alkanediols, comprising: providing a bio-1-alcohol and a catalyst treated with a base; dehydrating the bio-1-alcohol in the presence of the catalyst to form a bioalkene having a carbon chain of about 5 to about 20 carbon atoms and a bio-1-alkene regioselectivity of at least about 80%; and converting the bio-alkene to a bio-1,2-alkanediol having a carbon chain length of about 5 to about 20 carbon atoms. Preferably, the catalyst is treated with a promoter and then calcined.

The catalyst in this process may also be a γ-alumina catalyst and the base may comprise calcium. The γ-alumina catalyst is preferably treated with a calcium promotor and after treatment is calcined at a temperature of about 400° C. to about 500° C. The process preferably yields about 92% to about 99% of the bio-1,2-alkanediol.

The invention further includes a method for treating a catalyst for use in dehydration of alcohols, comprising providing a γ-alumina catalyst; treating the γ-alumina catalyst with a base, preferably a promoter as described herein, comprising a Group I or a Group II metal; and heating the γ-alumina catalyst to a temperature of about 400° C. to about 500° C., which is preferably done in a very controlled and deliberate manner. The base may comprise calcium, and preferably the base may be a calcium promoter and the heating occur during calcination. The calcium promoter may be used in an amount of about 0.01 weight percent to about 4 weight percent based on the weight of CaO determined after calcination, and more preferably in an amount of about 1 weight percent to about 2 weight percent based on the weight of CaO determined after calcination, preferably after careful calcination. The temperature during calcination in a preferred embodiment may be about 420° C. to about 480° C., and more preferably may be about 440° C. to about 460° C. Beneficial results are achieved based on the applicant's process including the preferred ranges noted. Applicant's determined that high calcination temperatures decrease catalyst regioselectivity and thus chemical yield of bio-1-alkene.

The invention further includes a composition, comprising at least one first bio-1,2-alkanediol having a carbon chain length of about 5 to about 20 carbon atoms which is synthesized by conversion of a first bio-alkene having a carbon chain of about 5 to about 20 carbon atoms and a bio-1-alkene regioselectivity of at least about 80%.

The composition may be a personal care composition, such as a hair care composition, an oral care composition, a skin care composition or a cosmetic composition.

The composition may also be a composition for a household product, such as a fabric care product or a cleaning product.

The composition may also be an industrial composition, or a pharmaceutical composition, a vitamin composition, or a health care composition.

In one embodiment of the composition herein, the composition may comprise a second bio-1,2-alkanediol, different than the first bio-1,2-alkanediol, the second bio-1,2-alkanediol having a carbon chain length of about 5 to about 20 carbon atoms which is synthesized by conversion of a second bio-alkene, preferably regioselectively, such that the resulting bio-alkene of about 5 to about 20 carbon atoms has a terminal bio-alkene content of at least about 80% and a bio-1-alkene regioselectivity of at least about 80%. The composition may comprise at least one other bio-compound different from the first and the second bio-1,2-alkanediols. In another embodiment, the composition may comprise an antimicrobial compound different from the first and the second bio-1,2-alkanediol and different from the other bio-compound. The composition may also further comprise at least one other bio-compound different from the at least one bio-1,2-alkanediol, and in another embodiment, such a composition may also further comprise at least one antimicrobial compound different from the at least one bio-1,2-alkanediol and different from the other bio-compound. The first bio-1-alkene in such composition preferably has a regioselectivity of about 92% to about 99% and more preferably about 95% to about 99%. The first bio-alkene may be a bio-octene and the at least one first bio-1,2-alkane diol may be a bio-1,2-octanediol.

Also included in the invention is a method for providing an antimicrobial effect to a composition, including incorporating an antimicrobial system to the composition, wherein the antimicrobial system comprises at least one first bio-1,2-alkanediol having a carbon chain length of about 5 to about 20 carbon atoms which is synthesized by conversion of at least one first bio-alkene having a carbon chain of about 5 to about 20 carbon atoms and a bio-1-alkene regioselectivity of at least about 80%. The antimicrobial system may further comprise a second bio-1,2-alkanediol different than the first bio-1,2-alkanediol, wherein the first bio-1,2-alkanediol has a carbon chain length of about 5 to about 20 carbon atoms and is formed by regioselectively converting a second bio-alkene, different than the first bio-alkene, having a carbon chain length of about 5 to about 20 carbon atoms and a bio-1-alkene regioselectivity of at least about 80%. The composition may further comprise at least one other bio-compound different from the first and the second bio-1,2-alkanediols, and in another embodiment may comprise at least one other preservative compound different from the first and the second bio-1,2-alkanediol and different from the other bio-compound. Such a composition may also further comprise at least one other bio-compound different from the at least one first bio-1,2-alkanediol. The antimicrobial may also further comprise at least one other antimicrobial compound and/or preservative compound different from the at least one first bio-1,2-alkanediol and different from the other bio-compound. The antimicrobial system may be made so as to demonstrate antimicrobial efficacy. The first bio-1-alkene preferably has a regioselectivity of about 92% to about 99%, and preferably about 95% to about 99%. The first bio-alkene may be bio-octene and the at least one first 1,2-alkane diol may be a bio-1,2-octanediol.

The invention further includes in one embodiment a method for boosting the antimicrobial efficiency of an antimicrobial and/or a preservative in a composition, comprising incorporating an antimicrobial system into the composition, wherein the second antimicrobial system comprises at least one first bio-1,2-alkanediol having a carbon chain length of about 5 to about 20 carbon atoms which is synthesized by regioselective conversion of a first bio-alkene having a carbon chain of about 5 to about 20 carbon atoms and a bio-1-alkene regioselectivity of at least about 80%. In the method, the antimicrobial system may further comprise a second bio-1,2-alkanediol different than the first bio-1,2-alkanediol, wherein the second bio-1,2-alkanediol has a carbon chain length of about 5 to about 20 carbon atoms and is formed by conversion of a second bio-alkene, different than the first bio-alkene, having a carbon chain length of about 5 to about 20 carbon atoms and a bio-1- alkene regioselectivity of at least about 80%. In the composition, it may further comprise at least one other bio-compound different from the antimicrobial and/or preservative and different from the first and the second bio-1,2-alkanediols. The composition may also further comprise at least one other bio-compound different from the at least one first bio-1,2-alkanediol. The first bio-1-alkene preferably has a regioselectivity of about 92% to about 99%., and more preferably about 95% to about 99%. In one embodiment, the antimicrobial system demonstrates antimicrobial efficacy. The first bio-alkene may be a bio-octene and the at least one first bio-1,2-alkane diol may be a bio-1,2-octanediol.

In yet a further embodiment, the invention includes an antimicrobial product, comprising at least one first bio-1,2-alkanediol having a carbon chain length of about 5 to about 20 carbon atoms which is synthesized by conversion of a first bio-alkene having a carbon chain of about 5 to about 20 carbon atoms and a bio-1-alkene regioselectivity of at least about 80%. The product may further comprise a second bio-1,2-alkanediol, different than the at least one first bio-1,2-alkanediol, the second bio-1,2-alkanediol having a carbon chain length of about 5 to about 20 carbon atoms and formed by conversion of a second bio-alkene, different than the first bio-alkene, having a carbon chain length of about 5 to about 20 carbon atoms and a bio-1-alkene regioselectivity of at least about 80%.

The antimicrobial product may further comprise at least one other bio-compound different from the at least one first and the second bio-1,2-alkanediols. In one embodiment, the product may further comprise a second antimicrobial and/or a preservative different from the antimicrobial product. The product may also further comprise at least one other bio-compound different from the at least one first bio-1,2-alkanediol, and may also further comprise a second antimicrobial and/or a preservative different from the antimicrobial product. The first bio-1-alkene preferably has a regioselectivity of about 92% to about 99%.

The antimicrobial product preferably also demonstrates antimicrobial efficacy. The first bio-alkene may be bio-octene and the at least one first 1,2-alkane diol may be a bio-1,2-octanediol.

The invention also includes a product for boosting the efficacy of an antimicrobial and/or a preservative in a composition, the product comprising at least one first bio-1,2-alkanediol having a carbon chain length of about 5 to about 20 carbon atoms which is synthesized by conversion of a first bio-alkene having a carbon chain of about 5 to about 20 carbon atoms and a bio-1-alkene regioselectivity of at least about 80%. Such product may further comprise a second bio-1,2-alkanediol, different than the at least one first bio-1,2-alkanediol, the second bio-1,2-alkanediol having a carbon chain length of about 5 to about 20 carbon atoms and formed by conversion of a second bio-alkene, different than the first bio-alkene, having a carbon chain length of about 5 to about 20 carbon atoms and a bio-1-alkene regioselectivity of at least about 80%. The composition of the product may also further comprise at least one other bio-compound different from the at least one first and the second bio-1,2-alkanediols, and also may further comprise at least one other bio-compound different from the at least one first bio-1,2-alkanediol. The first bio-1-alkene preferably has a regioselectivity of about 92% to about 99%. The first bio-alkene may be bio-octene and the at least one first bio-1,2-alkane diol may be bio-1,2-octanediol. The product preferably demonstrates antimicrobial efficacy.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
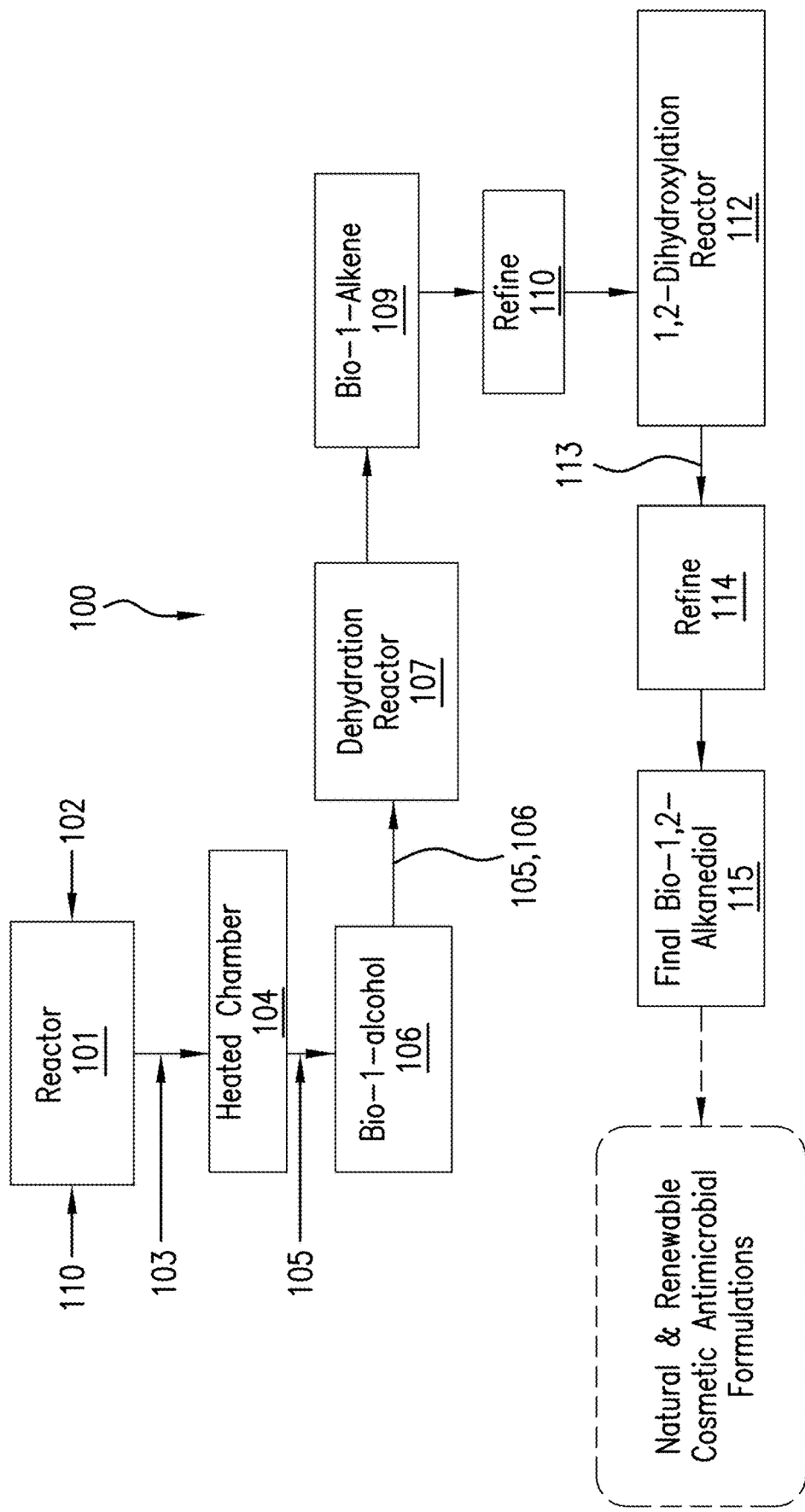
FIG. 1 is a process flow chart of steps in a preferred embodiment of a process described herein.
Figure 2:
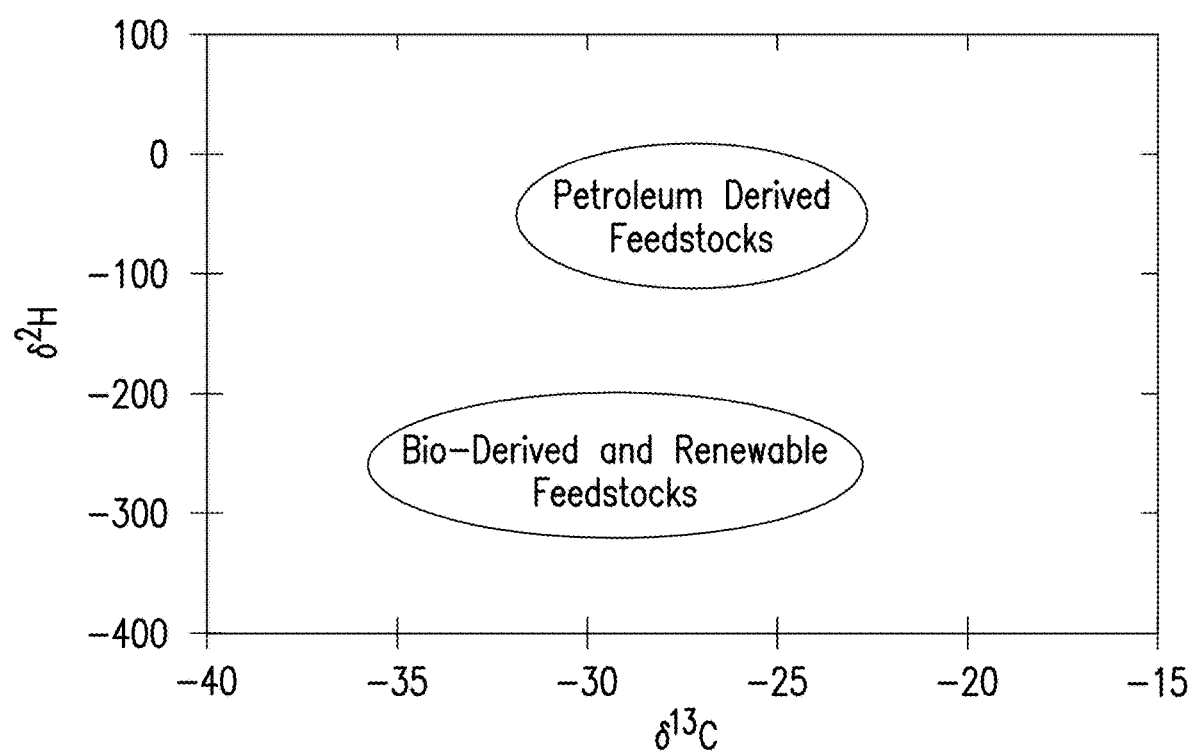
FIG. 2 is graphical representation of $\delta^2 H$ and $\delta^{13}C$ values for petroleum-based alcohols, alkenes and acids and the corresponding natural and renewable analogs.

The invention includes a process for the synthesis of bio-1,2-alkanediols. As used herein, "bio" when used with "alkanediol," or any specific alkanediol compounds noted within this class of compounds is intended to mean as described above that the compound, and preferably all of the carbons in the compound within this class of compounds, as described further below are "natural" compounds that are also authentic natural compounds derived from plant sources (algae-, plant-, animal- or biomass-derived) and are non-petrochemically derived (i.e., not derived from a non-renewable resource such as fossil fuel, petroleum or other "old" carbon source). In this sense, as they are derived from renewable materials, they are also sustainable compounds. It also means that such materials are formed from bio-alkenes. When used in the terms, "bio-alcohol," or "bio-alkene," and similar compounds herein, "bio" is intended also to have the same connotation as noted above for describing "bio-1,2-alkanediol." Such materials should preferably satisfy the requirements of having and being derived from an authentic or "new" carbon material (non-petrochemically derived) feedstock as confirmable through testing such a compound using mass spectroscopy as described above and/or gas chromatography, the current ASTM D6866-16 standard or prior methods such as specific stable isotope analysis (CSIA). The invention further includes the bio-1-alkenes and bio-1,2-alkanediols resulting from the synthesis process, as well as various products incorporating them. The invention further includes a method for treating a catalyst, which may be used in embodiments herein for dehydrating a bio-1-alcohol to form a bio-alkenes used in the processes herein for forming bio-1,2-alkanediols.

The invention provides efficient pathways to 100% "natural" or "bio" compounds that are from new carbon or authentic carbon materials that are not petrochemically derived and are preferably used in compositions and products that can be made for a wide variety of end uses and compositions, including as components of antimicrobial compositions and as cosmetic additives, among other uses described herein.

Also disclosed herein are methods of using bio-1,2-alkanediols for use as antimicrobials in a composition such as in or with an alternative preservation system and/or as hurdle technology. Also disclosed are various compositions comprising bio-1,2-alkanediols, including when used as an antimicrobial Also described are methods of boosting the antimicrobial efficacy of a composition already including a preservative or alternative preservation system, and the resulting boosted antimicrobial efficacy composition. Each of such methods includes incorporating into the composition a bio-1,2-alkanediol, combination(s) of at least two different bio-1,2-alkanediols, or combination(s) of at least one bio-1,2-alkanediol with at least one other bio-compound different from the at least one bio-1,2-alkanediol, wherein the bio-1,2-alkanediol(s) either act as a antimicrobial or boost the efficacy of another antimicrobial, preservative or other alternative preservation system already present in a composition. The bio-1,2-alkanediols may themselves be an antimicrobial product and/or a antimicrobial efficacy boosting product whether used alone, in combinations of one or more different bio-1,2-alkanediols, or in combination(s) of one or more different bio-1,2-alkanediols with at least one other bio-compound different from the bio-1,2-alkanediols and/or an optional, different antimicrobial, preservative or alternative preservation system. The bio-1,2-alkanediols when used in compositions herein exhibit antimicrobial efficacy.

In one embodiment herein, a process is described herein for synthesis of bio-1,2-alkanediols. As noted above, materials referred to herein as "natural" are intended to include materials that are non-petrochemically derived and are sustainable, whether synthesized from non-petrochemically derived, natural materials or formed from a natural, and preferably an authentic natural or bio-based source.

The method includes providing a bio-alkene having a carbon chain of about 5 to about 20 carbon atoms, preferably about 6 to about 14 carbon atoms, and more preferably about 6 to about 10 carbon atoms, with a bio-1-octene being preferred. The bio-alkene is preferably a bio-1-alkene with a traditional α-olefinic structure. It also preferably has a regioselectivity when prepared of at least about 80%, more preferably at least about 92% and most preferably at least about 95% up to as much as 99%.

Such bio-alkenes may be bio-1-pentene, bio-1-iso-pentene, bio-1-hexene, bio-1-heptene, bio-1-octene, bio-1-nonene, bio-1-decene, bio-1-dodecene, and related bio-1-alkenes up to chain length of 20 carbons. Larger or smaller bio-alkenes may also be made, however, the preferred bio-alkenes for use herein are those with sufficient chain length to serve as effective antimicrobials when converted to bio-1,2-alkanediols without losing the desired properties. Such bio-alkenes may be straight or branched chain molecules, although straight chain molecules are preferred and may include one or more functional or substituted groups for desired end effects in the end use application, for example, sulfonate groups, hydroxyl groups, ether groups, amide groups, carbonyl groups, carboxylic acid groups, amine groups, fluorinated groups, aryl or arene groups, and similar functional groups without intending to be limiting. Preferably any such functional or substituted groups do not interfere with conversion to an alkanediol or with the antimicrobial end application desired for the particular alkanediol.

Such bio-alkenes, such as bio-1-hexene and bio-1-octene, as are generated according to the invention, may be used to make bio-1,2-alkanediols as described herein, and may also be used to make other bio-based compounds and polymers, including, e.g., for synthesis of bio-based olefin copolymers. Bio-1-alkenes herein may be used, for example, in free radical or catalytic polymerization processes as are known in the art, to yield a variety of bio-polyalphaolefins homopolymers and copolymers, which are useful as lubricants and cosmetic ingredients. A further example, includes bio-linear low-density polyethylene (bio-LLDPE) can be prepared via copolymerization of bio-ethylene (derived via dehydration of sugarcane derived bio-ethanol to bio-ethylene) with bio-1-alkene copolymers yielding 100% renewable bio-LLDPE, a thermoplastic resin useful in film applications such as food and non-food packaging and shrink/stretch films.

The process of the invention includes an embodiment wherein the process makes bio-1,2-alkanediols, including providing a bio-1-alcohol and a catalyst treated with a base, preferably with a promoter and then calcined; dehydrating the bio-1-alcohol in the presence of the catalyst to form a bioalkene having a carbon chain length of about 5 to about 20 carbon atoms and a bio-1-alkene regioselectivity of at least about 80%; and converting the bio-alkene to a bio-1,2-alkanediol having a carbon chain length of about 5 to about 20 carbon atoms.

An overall flow diagram of a preferred process of making bio-1,2-alkanediols, that incorporates a preferred method of treating a catalyst as described further below is provided as embodiment 100 as shown in FIG. 1.

In the process generally referred to herein as process 100, in FIG. 1, prior to introducing the bio-1-alcohol, a catalyst is prepared. A suitable γ-alumina catalyst, e.g., $Al_2O_3$, 110 is introduced into a reactor 101 into which a calcium promotor or other base treatment material 102 as described further below is introduced. After a suitable treatment described in detail below, a modified catalyst 103 leaves reactor 101 and enters a heated chamber 104 such as an oven for heat treatment. If a catalyst promoter is used, for example, a calcination step occurs at preferred and controlled temperature ranges to increate a level of regioselectivity in a resulting bio-alkene in the next step. After, e.g., calcination in chamber 104, the calcined or otherwise heat-treated catalyst 105 is introduced along with a bio-1-alcohol 106 such as bio-1-hexanol or bio-1-octanol into a reactor 107 to promote intimate contact between the alcohol and the catalyst. Suitable reactors included fixed bed reactors, fluidized bed reactors, tubular reactors, and other suitable reactors. After sufficient time for dehydration of the bio-1-alcohol to a bio-alkene 109, which highly regioselects to a bio-1-alkene, a further, optional distillation or other purification or refining step in a column(s) or other equipment 110, may occur. The refined or otherwise purified and highly regioselective bio-alkene, which should be of a high quantity of bio-1-alkene, is then introduced to a reactor 112 in order to convert the bio-1-alkene into a bio-1,2-alkane diol 113. Such bio-1.2-alkane diol 113 may be further and optionally refined such as by distillation in a column(s) or through other steps in equipment 114. After purification or distillation, a final high yield of up to 99% is removed as the final bio-1,2-alkane diol 115.

The bio-1-alkene may be made using a catalytic process, and preferably using a catalyst that has been treated according to the method described herein. In one embodiment, the bio-alkene, which is preferably made herein to be of a high regioselectivity bio-1-alkene is formed using a bio-1-alcohol that is dehydrated by heating the bio-1-alcohol in the presence of a catalyst. This may be done, for example, by passing the bio-1-alcohol through a fixed bed reactor, or a fluidized bed reactor. The fixed bed may be packed with a catalyst, preferable a treated catalyst having been treated using techniques as described below.

For example, a bio-1-alcohol derived from a plant source, including biomass that can produce a related acid (e.g., 1-octanol may be derived from coconut, palm or other plant source or biomass that can produce octanoic acid, which is subsequently reduced via catalytic dehydrogenation to 1-octanol). The bio-1-alcohol is then dehydrated regioselectively by feeding the material at an elevated temperature into, e.g., a fixed bed reactor or other suitable reactor providing intimate contact between the bio-1-alcohol and the catalyst. The fixed bed may be packed with or otherwise arranged to provide sufficient contact with a catalyst. Other suitable reactors may be provided for this purpose provided they can achieve suitable contact for assisting in dehydration. Examples include tubular reactors, fixed and fluidized bed reactors, and the like.

The reactor can be designed as a simple heated reaction tube packed with catalyst and a flow of the gaseous bio-1-alcohol over the catalyst, preferably in a single pass affording greater than about 95% conversion, with greater than about 98% a preferred embodiment, and in all cases with no recycle stream used whatsoever in the overall process flow. In one embodiment, the reaction tube is heated isothermally, the tube having from 1 to 10 reaction zone temperatures along the length of the tube, each heated in the range of about 240° C. to about 360° C. in order to optimize catalyst performance. In a preferred embodiment, the reaction tube has 1 to 4 reaction zone temperatures in the range of about 260° C. to about 340° C.

In one embodiment the process is carried out in a fluidized bed reactor operated in the temperature range of about 240° C. to about 360° C. Other continuous flow reactor designs can be used in accordance with procedures and practices used by those familiar with the art of chemical engineering.

The catalyst used may be prepared by treating γ-alumina (e.g., Porocel® CatGuard®) with at least one base, preferably a promoter, such as with sodium hydroxide, potassium hydroxide, calcium acetate and the like to create a second catalyst. This second catalyst is then calcined to create a third catalyst. The calcination temperature has been found to be most unexpected and critical to creating the most effective catalyst. As seen below when calcined at about 500° C., a significant drop occurs in regioselectivity compared to catalysts calcined at lower temperatures. In one embodiment, as demonstrated in Table 1 below, preferred calcination temperature is about 400° C. to about 480° C., and a more preferred calcination temperature is about 440° C. to 460° C.

Varying catalysts may be used for assisting the bio-1-alcohol in the dehydration step. However, it is preferred that a suitable catalyst that can achieve high levels as regioselectivity as described herein is used. Suitable catalysts include γ-alumina-based catalysts and $ZnAl_2O_4$. Preferably, the catalyst is treated with a base, such as with sodium hydroxide, potassium hydroxide, calcium acetate and the like. In one preferred example, the catalyst is a γ-alumina catalyst treated with a base including a Group I or Group II metal. In one more preferred embodiment, calcium may be included in the base, and a calcium promoter used. After being treated with the calcium promoter to form a modified γ-alumina catalyst, in a further preferred embodiment, the modified γ-alumina catalyst is then calcined using varying calcination techniques but at temperatures which are preferably much lower than used in standard calcination methods to provide a calcined γ-alumina catalyst. The initial treatment provides a modified γ-alumina catalyst that is then calcined to be ready for use for varying processes including in the dehydration step of the processes herein for making bio-1-alkenes and their subsequent conversion to bio-1,2-alkandiols.

When employing a calcium promoter, it may be used in the treatment noted above in amounts of about 0.01 weight percent to about 4 weight percent, based on the amount of CaO determined after calcination. In preferred embodiments, about 1 weight percent to about 2 weight percent of the calcium promoter is used based on the amount of CaO determined after calcination.

In another embodiment, if desired, the alumina-based treated catalyst may be further organosilanized with an organosilane by treatment with, for example, diethoxydiphenylsilane to form an organosilanized base-treated γ-alumina catalyst. The organosilanzized base may be, for example, diethoxydiphenylsilane, dichlorodiphenylsilane and similar materials.

In one embodiment a catalyst support may comprise $ZnAl_2O_4$ and may also be modified by a base, e.g., by reaction with a promoter and similar catalysts and modified catalyst materials known or to be developed that are capable of carrying out the process as noted herein in a manner similar to the catalysts noted herein that can create a high level of regioselectivity could also be used.

The catalysts as noted above in addition to being suitable if treated with a base, may alternatively or also be treated with an organosilane or organosilane-modified material to create a promoter-modified catalyst. This promoted catalyst may be further organosilanized with an organosilane by treatment with diethoxydiphenylsilane to create a third, organosilanized and promoter-modified γ-alumina catalyst. The organosilane used to modify the catalyst may be, for example, diethoxydiphenylsilane, dichlorodiphenylsilane and similar materials. As seen in EXAMPLE 10 herein, silanization of the catalyst leads to a decrease in bio-1-octene selectivity, once again showing a difference from previous art and the direct and proven differences in the dehydration catalyst makeup necessary for a highly regioselective dehydration of 1-butanol or 1-octanol.

TABLE 1

| Catalyst | Calcination Temperature (° C.) | 1-Octene (%) | 2-Octene & 3-Octenes (%) | 1-Octanol (%) | 1-Octene Selectivity (%) |
| --- | --- | --- | --- | --- | --- |
| EXAMPLE 1 | 440 | 94.0 | 3.2 | 1.6 | 97.4 |
| EXAMPLE 2 | 500 | 88.9 | 6.6 | 3.5 | 93.1 |

In other treatment techniques herein, the γ-alumina catalyst may be modified by the technique of incipient wetting impregnation. A solution of the base is used to modify a solid support in a manner so as to avoid excess moisture that can result in support damage and chemical change. In one embodiment, the incipient wetting impregnation solution (IWS) is about 40% to about 100% the weight of the solid support, which may be, for example an untreated γ-alumina catalyst. In one embodiment, the untreated γ-alumina catalyst is selected from the commercially available, Porocel® CatGuard®. Preferably, the IWS is about 50% to about 60% of the catalyst support weight.

The γ-alumina may also be provided in a powder form having a surface area of about 50 to about 400 $m^2/g$. The γ-alumina in one embodiment is shaped by a suitable extrusion process, as are known to those skilled in this art of solid phase catalysts. In one example, the γ-alumina is in the form of 1/16" to 1/8" cylindrical rods with a length to diameter ratio of about 20:1, preferably about a ratio of about 5:1. The extrudate can be in the shape of spheres, star-shaped, hollow cylinders or any three-dimensional shape that can ultimately deliver a γ-alumina with sufficient surface area pore volume, mechanical strength, and physical size to be used in a continuous flow reactor system.

Once prepared, e.g., a base-treated, preferably a promoter treated, γ-alumina catalyst, as noted above is preferably calcined with care taken in regulating the temperature. This is done at an elevated temperature, preferably in a suitable chamber such as an oven, and the temperature range, while elevated to heat the materials, is not as high as calcination treatments typically used in prior catalyst processes. Instead, the temperature for calcination is kept at about 400° C. to about 500° C., and preferably about 420° C. to about 480° C., and most preferably about 440° C. to about 460° C. Typically, prior standard calcination treatments occur at temperatures 500° C. or higher with no limits established or specified for effectiveness. However, applicants discovered that by controlling this temperature and in the specific catalyst treatment process noted herein, the regioselectivity can be unexpectedly controlled to disproportionately favor formation of the bio-1-alkene when the bio-1-alcohol is dehydrated using the resulting calcined catalyst derived from a combination of catalyst treatment and a carefully controlled calcination process.

In the dehydration step herein, the bio-1-alcohol may be fed to a reactor undiluted or in water through the reactor. Optional an inert gas (e.g., nitrogen) may be used as a purge gas to retain consistency and avoid contaminates in the process. The bio-1-alcohol is preferably fed, such as by a pump (such as an HPLC pump) or pressurized gas source at a temperature of about 200° C. to about 400° C., although temperatures may be adjusted for different bio-1-alcohols depending on the reaction time and flow rate, the catalyst selected and the desired outcome. As the product is removed from the reactor, it is preferably monitored to determine content, identification of product and the ratio of bio-1-alkene conversion as well as the regioselectivity. In a preferred embodiment, the bio-1-alkene has a regioselectivity of at least about 80%, and more preferably about 92% to about 99% and even more preferably about 95% to about 99%.

In one embodiment, the dehydration process as described in FIG. 1 using the invention catalyst, i.e., the catalyst resulting from the preferred treatment and calcination process noted above, can be stopped and the catalyst maintained under inert gas flow for extended periods of time. This shutdown period can be hours, days or weeks, with heating or no heating applied during this period. The invention catalyst can be re-heated and dehydration process resumed without any detrimental effect on catalyst activity or regioselectivity. Thus, the invention catalysts are not only robust in continuous operation, but they can withstand periods of rest (inactivity) without negative effect on catalyst performance when brought back on line.

The bio-1-alkene may also be formed using a process in which the bio-1-alcohol in water is dehydrated by heating the bio-1-alcohol with a catalyst under a purge gas as noted above in a bulk process or other continuous reactor. Base and optional organosilane treatments may also be used as well as catalysts and reaction conditions such as those noted above, and most preferably, through use of a calcined γ-alumina catalyst formed by the process described above.

The bio-1-alcohol may also be formed using a process in which the bio-1-alcohol in water is dehydrated by heating the bio-1-alcohol with a catalyst under a purge, but as noted above, in bulk process or some other continuous reactor. Base and optional organosilane treatments may also be used as well as catalysts and reaction conditions as noted above.

Once the bio-1-alcohol is dehydrated to form the highly regioselective terminal, bio-1-alkene, that material is then converted to a bio-1,2-alkandiol having a carbon chain length of about 5 to about 20 carbon atoms. Prior to conversion, the bio-1-alkene may optionally be further refined such as by a distillation, vacuum distillation, fractionation or similar refining step to further purify the bio-alkenes to remove trace impurities and minor undesired fractions. For example, in forming a bio-1-octene, a C8 olefin content of about 90 weight percent to about 99 weight percent can be achieved, and at least about 95 weight percent and preferably about 97 weight percent or greater C8 olefin in the form of the n-α-olefin (i.e., 1-octene) can be achieved. In addition, in forming a bio-1-hexene, a C6 content of about 95 weight percent to about 99.8 weight percent can be achieved, with at least about 96 weight percent to about 99 weight percent thereof having a 1-hexene structure.

Various chemical reactions may be used for this conversion as are known for use in standard alkene to alkanediol conversions using petrochemically derived starting materials and/or that are used for smaller chain bio-alkanes. For example, the bio-1-alkene is reacted in the presence of at least one of formic acid or acetic acid, and a peroxide such as hydrogen peroxide to form an intermediate solution including a bio-1,2-epoxyalkane, bio-1,2-alkanediol, and other components. This is then further contacted with a base solution, such as a sodium hydroxide or another suitable base solution, to complete formation of the bio-1,2-alkanediol. The process noted above preferably yields about 60% to about 99%, and more preferably about 70% to about 99% or about 75% to about 99% of bio-1,2-alkanediol.

A bio-1-alkanol may also be converted to bio-1-alkene for use in this process by dehydrating the bio-1-alkanol using heat and an acid catalyst in accordance with other previous techniques.

Bio-1,2-alkanediols, having a chain length of about 5 to about 20 carbon atoms and synthesized by conversion of a first bio-alkene having a carbon chain of about 5 to about 20 carbon atoms and a bio-1-alkene regioselectivity of at least about 80%, more preferably 92% to about 99% and most preferably about 95% to about 99%. In one embodiment, a bio-1-alkanol having a carbon chain of about 5 to about 20 carbon atoms is preferably first converted to a bio-alkene regioselectively such that the resulting bio-alkene contains a bio-1-alkene content of at least about 80% or higher as noted above. Then the bio-1-alkene is converted to the 1,2-alkanediol by any known method known in the art. The resulting bio-1,2-alkanediol after conversion may be further refined such as by distillation, vacuum distillation, fractionation or other similar steps as are noted above for refining the bio-1-alkene to provide a refined, final bio-1,2-alkanediol.

Resulting bio-1,2-alkanediols, having a chain length of about 5 to about 20 carbon atoms are preferably synthesized by first deyhydrating a bio-1-alkanol having a carbon chain of about 5 to about 20 carbon atoms to a bio-1-alkene having a regioselectivity of at least about 80%, more preferably about 92% to about 99% and most preferably about 95% to about 99% of bio-1-alkene is formed, then treating the bio-1-alkene with formic or acetic acid in the presence of hydrogen peroxide, and further with an aqueous base solution. The bio-1,2-alkanediol may then be separated from the aqueous solution by any suitable technique known in the art of making dihydroxyalkanes in general, and more specifically 1,2-alkanediols. In a preferred embodiment, a distillation step is included for this purpose.

The bio-1,2-alkanediols as described above, may be used in a variety of compositions, whether used alone or in combination with other different bio-1,2-alkandiols according to the present invention. Such compositions may incorporate one, two or more different bio-1,2-alkanediols according to the invention herein that may act within an antimicrobial system. Such bio-1,2-alkanediol(s), may be used alone as an antimicrobial additive or in an antimicrobial system incorporating other bio-compounds (i.e., any suitable naturally derived, and preferably authentic natural product as tested using mass spectroscopy, gas chromatography and/or the ASTM standard noted above) such as bio-organic acids, bio-diols such as 1,3-propanediol, bio-1,2-butanediol, and 1,2-pentanediol that are extracts from fermentation products of bio-based starting materials and/or other antimicrobial materials, alternative preservatives, traditional preservatives or hurdle technology components as are known in the art or to be developed. An example of a preferred source of bio-compounds for use within the scope of the invention are trigylcerides. In yet a further example, another chemical group of bio-compounds that can be used in preparing alternative preservatives is commonly described as terpenoids. These natural terpenoids can have from 5 to 20 carbon atoms and can be readily obtained through sustainable farming practices and may be used within the scope of "bio-compounds" as that term is used herein for us in combination with the bio-1,2-alkanediols herein.

When used in a composition, the bio-1,2-alkanediols of the invention are preferably incorporated in an amount of about 0.1 to about 10 weight percent, and preferably 0.3 to about 2 weight percent, of the total composition; which amount may be varied depending on whether they are used alone for antimicrobial effect or with other components in an antimicrobial system. In the latter instance, the bio-1,2-alkanediols are preferably present in a ratio of the bio-1,2,alkanediol(s) to any other antimicrobial component(s) of about 99:1 to about 1:99, and preferably about 75:25 to about 25:75 in the antimicrobial system (wherein the system would include the bio-1,2-alkanediol(s) herein and/or any other antimicrobial, traditional preservative, alternative preservation and/or hurdle technology component(s) in the composition).

When used in certain compositions that are themselves viewed as "antimicrobial products" for providing to other formulators in various industries, the 1,2-bio-alkanediol(s) of the invention may be prepared initially as antimicrobial products that include one or more of the 1,2-bio-alkanediol materials made in accordance with the invention as described above and that incorporate one or more of the compositions as noted above, wherein such antimicrobial products may include also other bio-compounds, known antimicrobials, preservatives, alternative preservation materials or hurdle technology materials.

Examples of known preservatives and alternative preservative materials or compounds used in alternative preservation systems that may be used with the bio-1,2-alkanediols of the invention, include those suitable for use by various industries in which the present invention may be beneficial. For example, in the cosmetic and personal care industry, the bio-1,2-alkanediol(s) formed according to the present invention can be used alone, in combinations of two or more such materials and/or with other biocompounds and/or with known cosmetic preservatives and alternative preservation materials and/or hurdle technology components. Examples of preservative materials are listed by the FDA in the U.S. as including: (i) traditional preservatives, such as parabens (methyl, ethyl, propyl, and butyl), Quaternium 15 (aka "Dowicil"), diazolidinyl urea, imidazolidinyl urea, DMDM hydantoin, 2-bromo-2-nitropropane-1,3-diol (aka "Bronopol"), sodium hydroxyglycinate, phenoxyethanol, sorbic acid, potassium sorbate, methylisothiazolinone (aka "MI"), methylchloroisothiazoline (aka "CMI" often in combination with MI as Kathon CG), sodium benzoate, caprylyl glycol, sodium dehydroacetate, and formaldehyde; (ii) non-traditional or alternative preservatives: such as extracts of botanicals, organic acids, alcohols and glycerols, fermentation products, glyceryl caprylate, levulinic acid, p-anisic acid, eucalyptus globulus, glycyrrhiza, glabra (licorice) root extract, salvia officinalis, citrus grandis (organic grapefruit) extract, arnica montana (organic arnica) extract, boraxitrus seed extracts, leuconostoc/radish root ferment filtrate. goldseal (hydrastis canadensis root extract), citrus medica, limonum (Lemon) peel extract, caprylhydroxamic acid; and (iii) so-called "self-preserving" materials such as ethanol (when present at >15%), butylene glycol (when present at >10%), propylene glycol (when present at >20%); as well as (iv) other components used in alternative or traditional preservation systems in cosmetics such as MDM hydantoin, sodium hydroxymethylglycinate, benzisothiazolinone, benzyl alcohol, dehydroacetic acid, benzoic acid, salicylic acid, iodopropynyl butylcarbamate chloroxylenol, methyldibromo glutaronitrile, chlorphenesin, triclosan, benzalkonium chloride, chlorhexidine, polyaminopropyl biguanide, 5-bromo-5-nitro-1,3-dioxane (bronidox), hexamidine diisethionate, pentylene glycol, ethylhexylglycerin, triclocarban, glyceryl caprylate, o-cymen-5-ol, chlorphenesin, and glyceryl monolaurate, and traditional petrochemically-derived 1,2-alkanediols such as 1,2-hexanediol, 1,2-octanediol.

Other countries have similar lists with variations on the nature and type of preservatives, alternative preservatives or preservative system or hurdle technology additives that may be used in those countries. However, the present bio-1,2-alkanediols may be used in such other materials as well. In each of the above-noted systems and compositions, the preferred bio-alkene used in the invention is a bio-octene and the at least one first bio-1,2-alkanediol is bio-1,2-octanediol.

Examples of compositions that may benefit from an antimicrobial system incorporating one or more of the bio-1,2-alkanediols formed according to the process noted above and/or in compositions as noted above include personal care compositions, such as hair care, oral care, skin care or cosmetic compositions; household product compositions, such as fabric care or cleaning products; industrial compositions; and pharmaceutical, vitamin, nutraceutical or other health care compositions, any of which could benefit from an antimicrobial system, component or antimicrobial product derived from an authentic, natural, bio-based material.

The bio-1,2-alkanediols are preferably incorporated into a cosmetic or personal care composition (on a wet-basis or total weight basis) so as to make up about 0.001% by weight to about 25% by weight of the composition, and more preferably about 0.01% by weight to about 10% by weight of the composition. The amount used may vary depending on whether other hurdle technology components or other preservatives are also being used in the composition.

Such bio-1,2-alkanediols alone, in combinations of two or more different bio-1,2-alkandiols, and/or in antimicrobial systems incorporating the bio-1,2-alkanediol(s) alone or with other bio-compounds and/or other preservative, alternative preservative or hurdle technology components, may also be used in a method to provide an antimicrobial effect to a composition, wherein the compositions may be any of the variety of types of compositions as noted above. It is preferred that the bio-1,2-alkanediols herein provide an antimicrobial effect and efficacy to a composition into which the bio-1,2-alkanediols are incorporated, whether into a personal care, household, industrial, pharmaceutical, vitamin, nutraceutical or other health care composition. Such an antimicrobial effect may be demonstrated by using a variety of suitable antimicrobial effectiveness tests (AET). Such tests include, for example, a compendial test performed during formulation development and stability testing in parenteral drug products intended as a multi-dose product. Suitable test procedures and acceptance criteria are described in the *U.S. Pharmacopeia*, AET, the *European Pharmacopeia* (Efficacy of Antimicrobial Preservation), and the *Japanese Pharmacopeia* (Preservation Effectiveness Tests). Other suitable challenge tests may be used. The FDA also recommends suitable challenge testing.

One group of antimicrobials, some of which are in the group noted above, are other alcohols, and preferably at least one other alcohol, preferably at least one other diol, and most preferably one or more other vicinal diols that may be petrochemically derived, albeit, it is preferred that such materials are used a diluents or in smaller amounts for providing some antimicrobial effect, but are not so great as to diminish the impact of the natural, bio-based 1,2-alkane diols of the present invention. By the term, "vicinal diols," it is meant materials that have hydroxyl groups which are bonded to atoms in the molecule which are next to each other, i.e., wherein two atoms each bearing a hydroxyl group are bonded to each other. Examples of vicinal diol compounds suitable for use in the invention, include, but are not limited to, ethylene glycol and propylene glycol. Such materials are used in the personal care, cosmetic and pharmaceutical arts as humectants and solvents, and as described in U.S. Publication No. 2007-0207105-A1 as having some modest antimicrobial activity.

Preferred vicinal diols for use with the bio-1,2-alkanediols herein, in compositions described for use in personal care and pharmaceutical use compositions are medium-chain length, linear vicinal diols that demonstrate some antimicrobial activity including petrochemically-derived 1,2-pentanediol, 1,2-hexanediol, 1,2-octanediol, and 1,2-decanediol. Other vicinal diols useful in the compositions described herein include molecules derived from glycerin. Glycerin can be reacted with other molecules at its 1- or 3-position, leaving two vicinal hydroxyl groups. For example, glyceryl monoethers, such as ethylhexylglycerin [3-(2-ethylhexyloxy)propane-1,2-diol], available commercially as SENSIVA®SC50 from Schulke & Mayr, are useful, traditional, liquid vicinal diols having antimicrobial properties. Glyceryl monoesters such as glyceryl monolaurate, glyceryl mono caproate, or glyceryl monocaprylate, the latter of which is commercially available from Inolex Chemical Company, Philadelphia, Pa., are also useful antimicrobial vicinal diols. For the preservation of cosmetics, toiletries and pharmaceuticals, vicinal diols are known to be effective against bacteria and yeast but weak against fungi and to date there are only limited natural choices, none of which to applicant's knowledge are bio-derived natural 1,2-alkanediols of from 5 to 20 carbon atoms.

The compositions herein preferably do not include, or include only to a minor amount any preservation materials such as parabens, or other known preservation materials that can be viewed as harmful to the user.

Such personal care and pharmaceutical compositions may optionally further include a solubilizing agent in amounts of about 1% to about 70% by weight of the combination of the solubilizing material with the bio-1,2-alkane diol(s) (or if used with other preservation component(s) by weight of the entire antimicrobial system with the solubilizing material). Suitable solubilizing agents include vicinal and other traditional diols.

Also useful in with the bio-1,2-alkanediols in any antimicrobial system are hydroxamic acid and the like which may be used in a variety of industries. Suitable hydroxamic acids include alkylhydroxamic acids and bio-alkylhydroxamic acids that include at least one alkyl group of a chain length of about two to about twenty-two carbon atoms, which may be branched or linear in structure, substituted or unsubstituted, and saturated or unsaturated as noted hereinabove. Preferred alkylhydroxamic acids contain alkyl groups of a chain length of about six to about twelve carbon atoms and most preferably linear chains of that length. Most preferred alkylhydroxamic acids are caprylohydroxamic acid, having a linear terminal chain of eight carbon atoms and caprohydroxamic acid, having a linear chain of ten carbon atoms. Such alkylhydroxamic acids may be used alone or in combination and in amounts as noted above for an optional solubilizing agent.

Formulations prepared for personal care use, and pharmaceutical compositions, depending on the end use (topical or oral) may include any other colorants, fragrances, active ingredients or other additives typically used and/or to be developed in the art for use in personal care and pharmaceutical formulations, in which additives will vary depending upon the formulation in which the preferred bio-1,2-alkanediols, or antimicrobial products or systems containing the bio-1,2-alkanediols are used, for example, in topical skin toners, skin cleansers, night creams, skin creams, shaving creams, skin care lotions, or other cosmetic preparations; make-up, such as foundation, liquid and powder-based make-up, mascara, lipstick, blush, gloss, eye-liner and the like; or other personal care and/or pharmaceutical compositions, such as, sunscreens, lip balms, fragrances, massage oil, shampoos, conditioners, conditioning shampoos, hair styling gels, hair reparatives, hair tonics, hair fixatives, hair mousses, bath and shower gels, liquid soaps, moisturizing sprays, makeup, pressed powder formulations, bath additives, ophthalmic preparations, foaming soaps and body washes, sanitizing wipes, hand sanitizers, medicaments (tablets or liquid), towelettes and wipes and others. It should be understood, based on this disclosure that a wide variety of personal care and pharmaceutical compositions could benefit from the properties of the bio-1,2-alkanediols of the present invention, wherein, as used herein, pharmaceutical composition is one having at least one active pharmaceutical ingredient (API).

The personal care and pharmaceutical formulations, if liquid based (such as gels, hydrogels, lotions, shampoos, liquid pharmaceuticals and the like) will also preferably include water as part of the liquid base. The formulations and compositions may include other additives as well depending on the end formulation desired, such as without limitation, at least one humectant, at least one emulsifier and/or thickener, chelating agent(s), gelling agent(s), amino acid(s), emollient(s), various solvents, free radicals and initiators, sunscreen UVA and/or UVB blocking agents, antioxidants, other preservatives, waxes, polymers and copolymers, inorganic and organic pigments and/or one or more fragrances, favoring(s), coloring agent(s), herbs, natural extracts, essential oils, pharmaceutical drug products, other APIs and other additives commonly used in such formulations.

Personal care and pharmaceutical compositions using the bio-1,2-alkanediols herein may be lotion-based, oil-in-water emulsions, water-in-oil emulsions, water-in-silicone emulsions, silicon-in-water emulsions, gels, solids, liquids, cream based, oil based, aqueous/alcoholic or glycolic solution based, dispersions, suspensions or syrups, microemulsions or a liposome-based formulations.

In water-based formulations, other than solids and thicker gels, etc., it is preferred that about 20% by weight to about 95% by weight (on a wet basis) of water is incorporated therein. The various additives aside from the water and preferred antimicrobial systems noted herein, would make up the remaining portion of various personal care and pharmaceutical compositions. Preferably, each additive is present in an amount of up to about 75 percent by weight of the entire formulation, and more preferably up to about 40 percent by weight, with a collective amount of such additives of preferably no greater than about 50 percent by weight.

In a household product, antimicrobials are also useful additives. Household product compositions can include household cleaners as well as fabric care compositions. Cleaning compositions (whether solids or solutions) can incorporate cleaning agents that are active ingredients for cleaning (bleach, vinegar, ammonia, citric acid and the like). For liquid cleaning agents, aqueous solutions may be used as are known in the art or to be developed, such as quaternary ammonium compounds, bleach, vinegar, or basic or acidic cleansers. Commercially available quaternary ammonium-based cleaning products include various antibacterial all-purpose cleaners among others which are intended and well-suited for sanitizing or disinfecting efficacy, however, such compositions still incorporate antimicrobials and other preservatives for shelf life and to prevent growth of foreign agents. Thus, such compositions also benefit from use of the natural bio-1,2-alkanediols herein.

For more natural cleaning solutions, such as citric acid-based agents or other green cleaning agents (ecologically friendly), consumers would be interested in further additives that are also natural, and in this case that are derived from a biological source. Thus, such compositions benefit from natural bio-based 1,2-alkanediols herein as well as antimicrobial systems and products incorporating the bio-1,2-alkanediols. Such natural cleaning compositions as well as standard cleaning compositions as noted above may also incorporate various optional additives in varying amounts as noted below. Citric acid-based cleaning products may include lemon, orange or grapefruit-based cleaning agents.

Other suitable components may include grape seed oil, vegetable oils combined with one or more of mild peroxide agents, surfactants, and the like, as well as pigment(s) or colorant additive(s) to provide a visual alerts when the cleaners are present, conventional or alternative preservation compound(s), antimicrobial(s), bactericide(s) or fungicide(s) (each of which may be used along or in combination with the bio-1,2-alkanediols of the present invention in an antimicrobial system or product), thixotropic agents and rheological modifiers, pH adjusting additives or buffers, as well as fragrance additive(s) for providing a clean smell (pine scent, lemon scent, orange scent, floral scent, etc.). In addition, other agents for foaming, color change or effervescence (bubbling) may be provided if desired to demonstrate cleaning action. Solid cleaners can incorporate similar additives, but can be compressed, incorporated or formed from depositing a cleaning material on a substrate (sponge, scrubber, mop head or the like), and various inactive agents for holding the solid cleaning material together (hardeners, gelling agents, mineral powder and the like). Other additives for household cleaning compositions may include pH buffering agent(s), a fragrance encapsulate(s) or carrier(s), fluorescer(s), hydrotrope(s), soil-release agent(s), polyelectrolyte(s), enzyme(s), optical brightening agent(s), anti-oxidant(s), UV absorbing compound(s), propylene glycol, dipropylene glycol, opacifier(s), pearlescent(s) and combinations of these as well as other cleaning product additives known or to be developed.

The fabric care compositions can include any active fabric cleaning component as well as various conditioning components as are known or to be developed in the art. Such compositions may include ingredients used for fabric cleaning or laundering, fabric conditioning or softening, fabric dye(s), water conditioner(s) and/or fabric care composition(s) such as spot removers or stain treatments. Such ingredients include without limitation antifoam agent(s), antideposition agent(s), fragrance(s) and their carrier(s) or encapsulate(s), traditional or conventional diols (although such diols may be omitted if the bio-1,2-alkanediols are useful in the same or an enhanced or boosted capacity for an existing diol), colorant(s) such as pigment(s) or dye(s), and co-softening agent(s). Others additives for fabric care compositions may include, without limitation, other traditional preservative(s), antimicrobial(s), bacteriocide(s), and/or fungicide(s)(each of which may be used alone or in an antimicrobial product or system as described herein), pH modifier(s) or buffering agent(s), fluorescer(s), hydrotrope(s), soil-release agent(s), polyelectrolyte(s), enzyme(s), optical brightening agent(s), anti-shrinking agent(s), anti-wrinkle agent(s), anti-spotting agent(s), anti-oxidant(s), UV absorbing compound(s), anti-corrosion agent(s), drape imparting agent(s), anti-static agent(s), ironing aid(s), odor-preventing compound(s), perfume encapsulate(s), cotton seed oil, tea tree oil, aloe vera extract, propylene glycol, dipropylene glycol, opacifier(s), pearlescent(s) and combinations of these components.

The antimicrobial bio-1,2-alkanediols herein may also be used in the treatment of the finished textile(s) and/or treatment of the fibers or yarns from which a textile is to be fabricated to achieve the desired benefit. Textiles may include woven and non-woven textiles, such as felt and tapa cloth and other bark cloths, or blends and combinations of the same. Textile fiber (whether it exists in finished textile form, yarn or fiber form) may be any known or developed in the art and include synthetic fibers, "natural" fibers, such as animal derived fibers or cellulosic/plant-derived fibers and blends or combinations of any of these.

Animal-derived fibers may include and derived from the hairs or fur of an animal. Examples are, without limitation, lambs or sheep's wool, alpaca, angora wool, azlon, byssus, camel hair, cashmere wool, chiengora, chatgora, llama, mohair wool, qiviut, rabbit, silk, vicuna, yak, pashmina wool and combinations of the same. Cellulosic or plant-derived fibers may include, without limitation, those obtained from flax (linen fibers), cotton, ramie, jute, kenaf, beach hibiscus, roselle, urena, hemp (e.g., Crotalaria juncea, Cannabis sativa, Apocynum cannabinum), hoop vine, sisal, henequen, yucca, abaca, genus *Sansevieria*, New Zealand flax, cotton, coir, milkweed, kapok, floss silk, Proboscidea parviflora, bamboo, bast, Pique, banana, modal, lyocell, pina, raffia, rayon, soy protein, acetate and combinations of the same. Synthetic fibers may include any known or to be developed, such as for example, and without limitation, acrylic, Kevlar®, modacrylic, Nomex®, nylon, polyester, lycra, spandex, rayon, and combinations of the same.

Fabric treatment compositions may be applied to the textile or fibers. The compositions may be applied as either a wet or dry composition and during a laundering cycle with water or a drying cycle. Such fabric treatment materials may be used for softening and/or conditioning a textile or fiber; reducing and/or preventing wrinkles, imparting fragrances to a textile or fiber; reducing ironing time, improving softness and the like.

The invention also incorporates use of the 1,2-bio-alkanediol materials formed according to the invention as a material for boosting the antimicrobial efficiency of existing antimicrobials, preservatives, alternative preservation materials and/or hurdle technologies.

By boosting the antimicrobial efficacy, it is meant that the antimicrobial efficacy of an existing antimicrobial and/or preservative (including alternative preservation materials or hurdle technologies) when combined with the 1,2-bio-alkandiols achieve an improvement of antimicrobial effectiveness that is more than insubstantial, i.e., at least about 5%, preferably at least about 10%, and more preferably at least about 20% or more improvement, while providing a natural boosting material. Boosting effects and antimicrobial effects in a formulation are evaluated by measuring performance using a preservative efficacy test ("PET") or a challenge test. Preservatives and antimicrobials used in cosmetic, toiletry and pharmaceutical products must enable the products to successfully pass microbiological testing protocols, known as "challenge tests," established by government regulations and trade organizations. Challenge tests are performed by adding known quantities of microorganisms to a product and measuring the increase or decrease in microorganism population over time. The organisms include Gram-positive bacteria, Gram-negative bacteria, yeast and mold. The Cosmetic, Toiletries, and Fragrance Association (CTFA) has defined a challenge test that is widely accepted as the standard in the cosmetic, toiletry and pharmaceutical industry. The test requires that the quantity of bacteria be reduced by 99% in seven days, and that the quantity of yeast and fungi (mold) be reduced by 90% in seven days. In order to pass a challenge test, the product must contain the appropriate amounts and types of preservative compounds that will enable antimicrobial efficacy against a broad spectrum of microorganisms in a short period of time.

In addition to the content noted to provide antimicrobial efficacy, if using as a boosting material to improve the effectiveness of an existing antimicrobial and the like as noted above it is preferred that the 1,2-bioalkanediol(s) are incorporated in an amount of about 0.1 to about 10 weight percent, and preferably 5.0 to about 3.0 weight percent, of the total composition; and in a ratio of about 99.999:0.001 to about 0.001:99.999, and preferably about 99.9:0.1 to about 0.1:99.9 of the total amount of existing antimicrobial, preservative, alternative preservation and/or hurdle technology components already existing in the composition.

The invention will now be described with respect to the following non-limiting examples:

EXAMPLES

Bio-1-octanol is formed from the hydrogenation of bio-octanoic acid (suitable sources of which may be derived from coconut, palm or any other renewable source or process that can produce octanoic acid). The bio-1-octanol is dehydrated regioselectively by feeding the bio-1-octanol at an elevated temperature into a fixed bed reactor containing a catalyst according to the invention herein.

Gas Chromatography (GC) was an important method used to characterize both petroleum and natural-renewable derivatives. Products (e.g. octenes) were characterized using a Thermo Scientific Trace 1310 Gas Chromatograph employing an FID detector and Chromeleon software (version 7.2.4.8525). For dehydration reactions products the GC employed a Restek MXT-5 column (30 m length, 0.5 μm film, 0.53 ID), helium carry gas (3.0 mL/min), CT split injection 45 mL/min (5.0 mL/min purge flow), injector 250° C., detector 300° C., oven 70° C. hold for 8 min, then ramp to 300° C. (15° C./min) with a final hold for 6.67 min. For alkanediol products GC analysis employed a Restek MXT-WAX column (30 m length, 0.5 μm film, 0.53 ID), helium carry gas (5.0 mL/min), CT split injection 10 mL/min (5.0 mL/min purge flow), injector 220° C., detector 250° C., oven 70° C. hold for 0.25 min, then ramp to 250° C. (10° C./min) with a final hold for 6.67 min.

Example 1

γ-Alumina powder was treated with an aqueous solution of calcium acetate using the technique of incipient wetting to afford a catalyst containing 1.50% calcium (based on CaO) after calcination in air at 440° C. for a period of 12 h.

Example 2

γ-alumina powder was treated with an aqueous solution of calcium acetate using the technique of incipient wetting to afford a catalyst containing 1.50% calcium (based on CaO) after calcination in air at 500° C. for a period of 12 h.

Example 3

Catalysts prepared in EXAMPLE 1 and EXAMPLE 2 were loaded into separate 75 mL (Sigma Aldrich Part No. Z173592) reactors, each was wrapped with heating tape and covered with fiberglass insulation. The temperature was controlled by affixing a thermocouple to the outside skin of the reactor, this input was used for a temperature controller. Bio-1-octanol was fed into the reactor maintained at 315° C. using an HPLC pump. The bio-1-octanol feed rate was adjusted in a manner to obtain conversion more than 95%, but less than 100%. After 1 h of continuous operation a sample was collected and analyzed for analyzing chemical conversion of the bio-1-octanol and regioselectivity of bio-1-octene. The results are shown below:

TABLE 2

| Catalyst | Calcination Temperature (° C.) | 1-Octene (%) | 2-Octene & 3-Octenes (%) | 1-Octanol (%) | 1-Octene Selectivity (%) |
|---|---|---|---|---|---|
| EXAMPLE 1 | 440 | 94.0 | 3.2 | 1.6 | 97.4 |
| EXAMPLE 2 | 500 | 88.9 | 6.6 | 3.5 | 93.1 |

Example 4

γ-alumina in the form of 1/16" extrudate, Porocel® Cat-Guard® was cut to have length to diameter ratios in the range of 2 to 4. The extrudate was modified with an aqueous solution of calcium acetate. The weight of solution to alumina was 0.55 by weight and the calcium acetate concentration was at level to deliver 1.50% of CaO (after calcination). This catalyst was subjected to calcination in air at 440° C. for a period of 12 h.

Example 5

Figure 3:
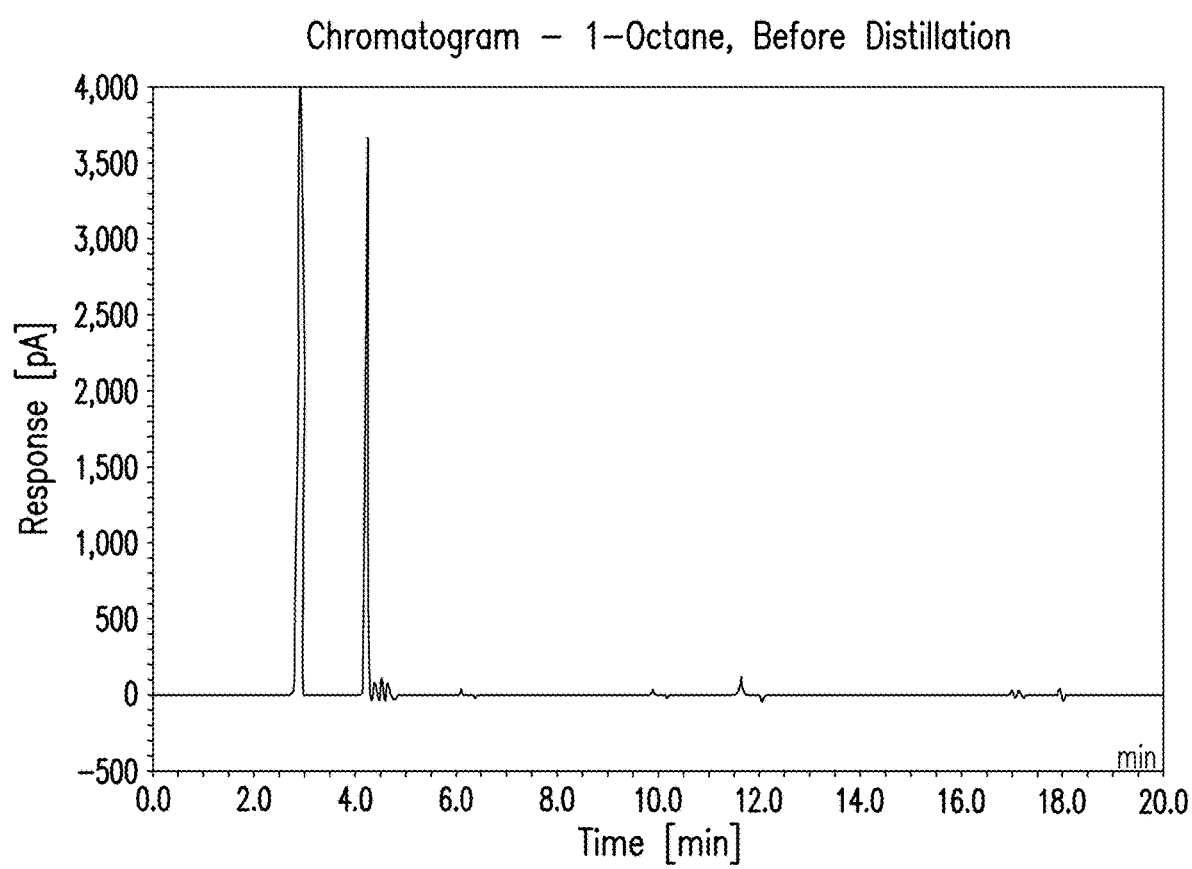
FIG. 3 is the Gas Chromatograph (GC) chromatogram of the reactor output from the dehydration of bio-1-octanol using the catalyst prepared in Example 4 at 0.2 ml of bio-1-octanol feed and heated to 315° C.

The 48 g of the catalyst prepared in EXAMPLE 4 was loaded into a 75 mL (Sigma Aldrich Part No. Z173592) reactor, wrapped with heating tape, and covered with fiberglass insulation. The temperature was controlled by affixing a thermocouple to the outside skin of the reactor, this input was used for a temperature controller. Bio-1-octanol was fed at 0.2 mL/min into the reactor maintained at 315° C. After >1,400 h of TOS, that included regular shut-downs and start-ups, catalyst performance with regard 1) chemical conversion of the bio-1-octanol, 2) product selectivity, 3) and regioselectivity for bio-1-octene was unchanged. A GC chromatogram of the crude product collected from the reactor is shown in FIG. 3 with an octene selectivity of 96% and with chemical yield of bio-1-octene of 94%.

Example 6

Figure 4:
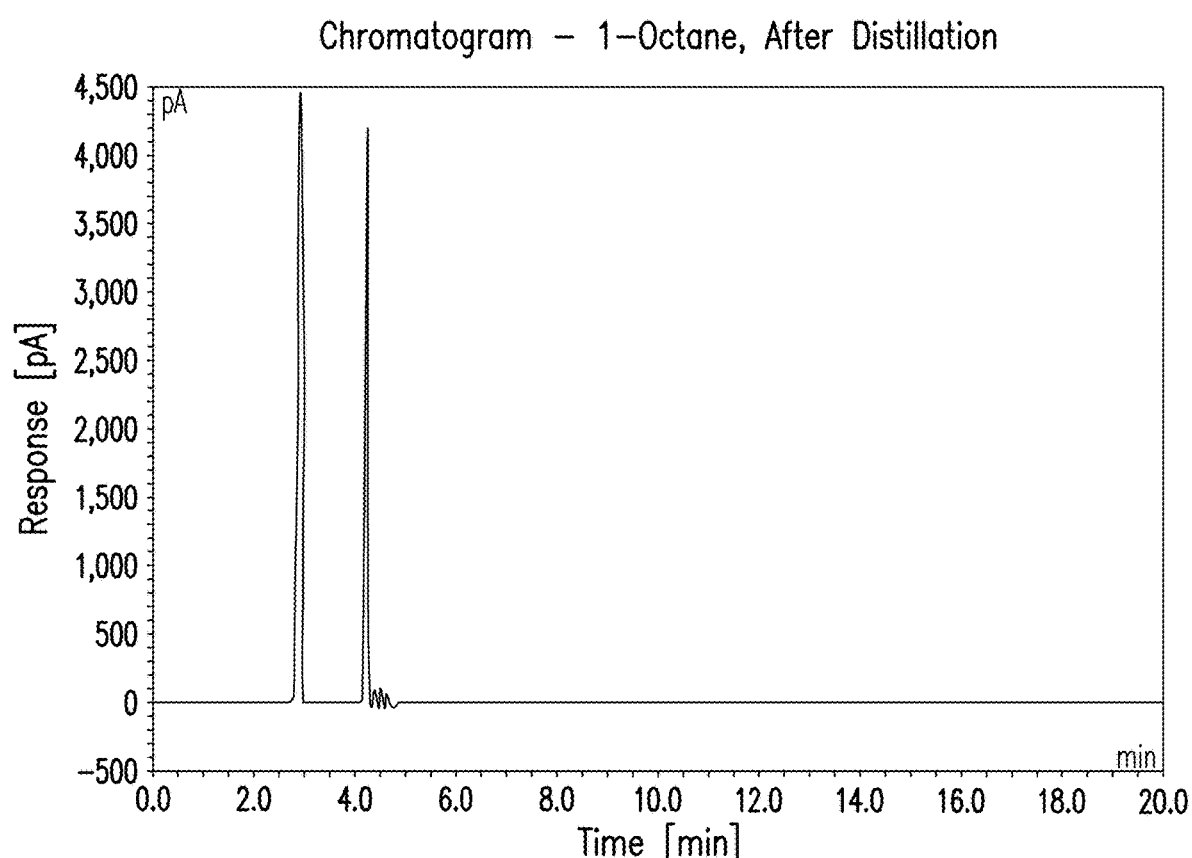
FIG. 4 is the GC chromatogram of the bio-1-octene obtained from the reactor after distillation.

The product in EXAMPLE 5 was subjected to simple distillation at atmospheric pressure. The product obtained was analyzed by GC and the chromatogram is shown in FIG. 4. The product from the distillation was 99.9% bio-octenes with a 96.7% content of bio-1-octene.

Example 7

Figure 5:
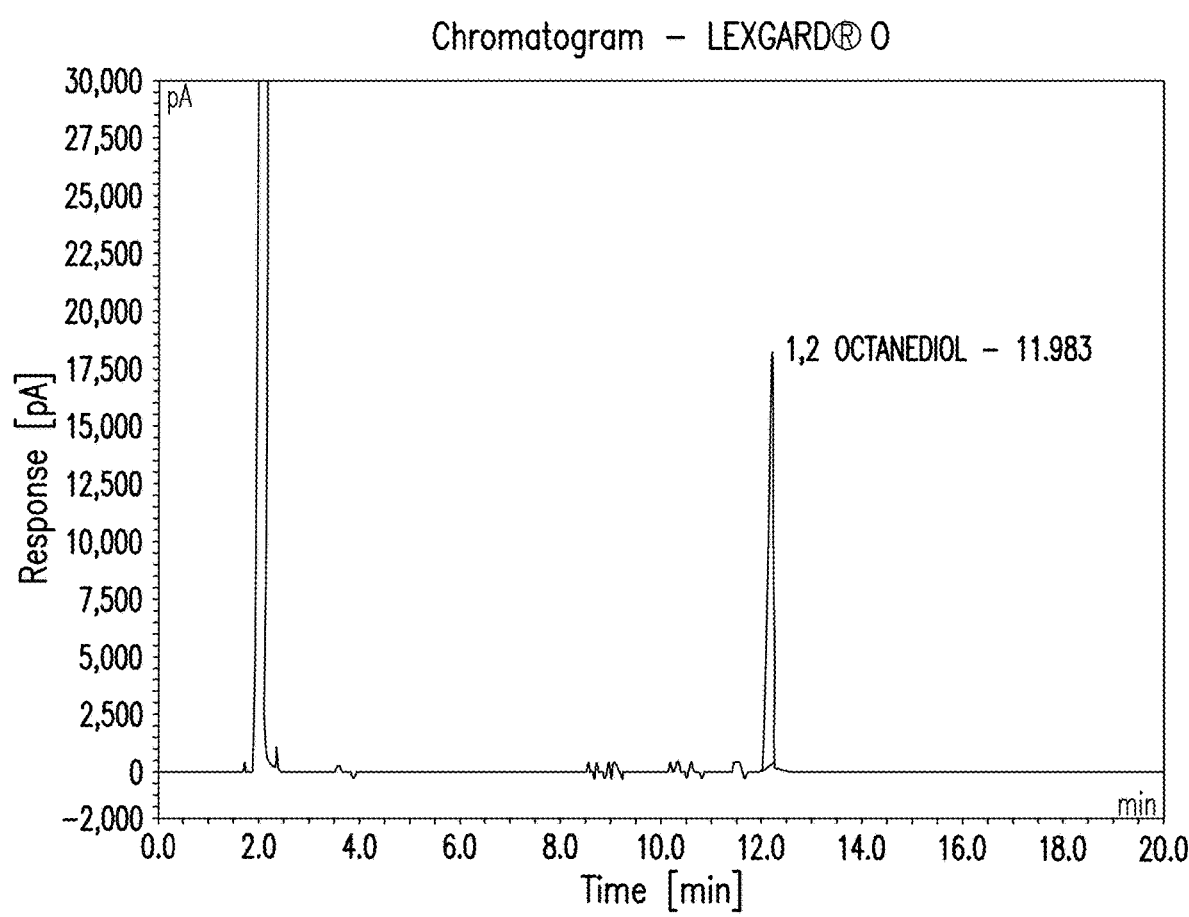
FIG. 5 is the GC chromatogram of the bio-1,2-octanediol obtained from dehydration of bio-1-octene, conversion to the 1,2-octanediol and then fractional distillation of the 1,2-octanediol.
Figure 6:
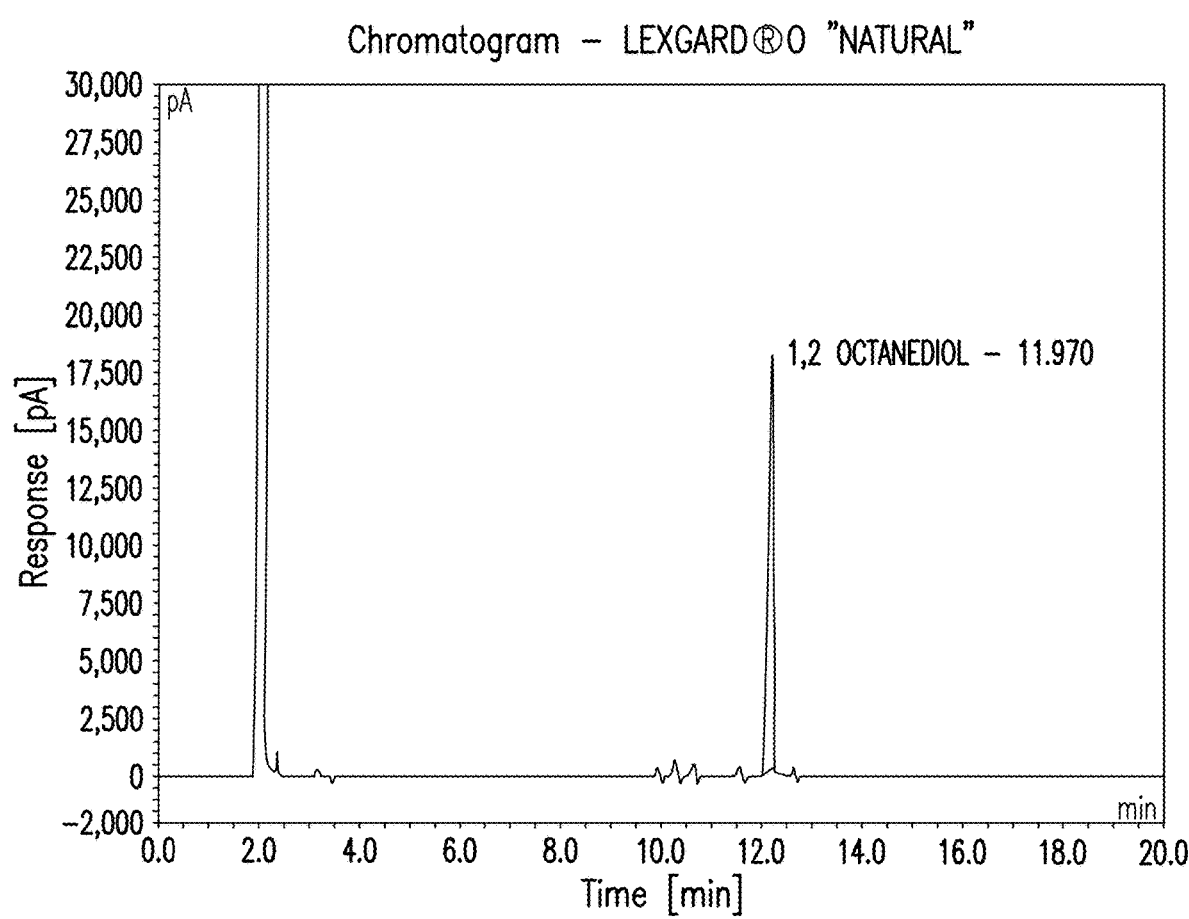
FIG. 6 is the GC chromatogram of the petro-1,2-octanediol currently approved for use in cosmetic formulation.

The product in EXAMPLE 6 was converted to the bio-1,2-octanediol by treatment with formic acid and peroxides, then a base hydrolysis, and finally purified by fractional distillation. The GC chromatogram is shown in FIG. 5. The bio-1,2-octanediol obtained in this example has a chemical purity 98.7% by GC analysis. A typical GC chromatogram of the petro-1,2-octanediol currently used in commercial cosmetic applications is displayed in FIG. 6.

Example 8

Stable isotope analyses were carried out on petroleum-based and those prepared from the natural and renewable feedstocks prepared in EXAMPLES 6 and 7. The values are shown below:

TABLE 3

| Compound | $\delta^{13}C$ | $\delta^2H$ |
|---|---|---|
| Bio-1-Octanol | 32.3 | −273 |
| 1-Octanol (petro-based) | 30.3 | −87 |

TABLE 3-continued

| Compound | $\delta^{13}C$ | $\delta^2H$ |
|---|---|---|
| Bio-1-Octene | 32.0 | −288 |
| 1-Octene (petro-based) | 31.8 | Not tested |
| Bio-1,2-Octanediol | 32.2 | −245 |
| 1,2-Octanediol (petro-based) | 31.5 | −50 |

Example 9

The bio-1,2-octanediol prepared in EXAMPLE 7 was subjected to testing that is currently used to qualify the petroleum, non-renewable, non-natural equivalent. The bio-1,2-octanediol prepared in EXAMPLE 7 was found to meet all the batch analytical testing requirements:

TABLE 4

| Analysis | Natural 1,2-octanediol | Petroleum 1,2-octanediol | Specification |
|---|---|---|---|
| Odor | Conforming | conforming | mild |
| Color, Lovibond (yellow) | 0.1 | 0.1 | ≤1.5 |
| Color, Lovibond (red) | 0.0 | 0.0 | ≤0.3 |
| Sediment | Conforming | Conforming | No discoloration |
| Color, APHA 142 | 8 | 1 | ≤100 |
| COLOR, APHA 142-01 | 8 | 1 | ≤30 |
| Infrared Spectrum | Conforming | Conforming | Matches Std. |
| Hydroxyl value Mg KOH/g | 761 | 740 | 740 to 770 |
| Moisture % w/w | 0 | 0 | ≤2 |
| Appearance | Conforming | Conforming | Clear liquid above 35° C. |
| Assay, % | 98.7 | 99.5 | ≥98.0 |
| % 1,2-octane oxide | 0.1 | 0.1 | Report result |
| Color 999-03 | Conforming | Conforming | Matches Standard |

Example 10

In a comparative example, bio-1-octanol was fed into a 75 mL reactor packed with a catalyst prepared as follows: gamma-alumina powder was modified with a sodium hydroxide solution (5 wt-% NaOH) to create a second catalyst, the second catalyst was dried in an oven and then treated with diethoxydiphenylsilane (1 wt-% based on alumina) dissolved in ethanol. The solvent was removed, the catalyst washed with ethanol, and dried in an oven to create a third catalyst. This third catalyst was calcined at 400° C. for 12 h. The catalyst was loaded into a 75 mL reactor, heated to a target temperature of 325° C. and bio-1-octanol feed rates were adjusted to optimize both conversion and regioselectivity.

Example 11

Petro-1-hexanol was fed into a 75 mL reactor packed with the catalyst prepared in EXAMPLE 4. The catalyst used in this example had greater than 1,400 h of TOS used for bio-1-octanol dehydration to bio-1-octene. For this series of dehydration reaction examples, the temperature was varied from 330° C. to 370° C. and the feed rate was adjusted in order to achieve between 1 and 2% of hexanol passing through the reactor. The results for the hexanol dehydration are shown below:

TABLE 5

| Catalyst | Reactor Temperature (° C.) | 1-Hexene (%) | 2-Hexenes & 3-Hexene (%) | 1-Hexanol (%) | 1-Hexene Selectivity (%) |
|---|---|---|---|---|---|
| EXAMPLE 11A | 330 | 92.8 | 3.5 | 1.8 | 95.8 |
| EXAMPLE 11B | 350 | 93.8 | 3.1 | 1.7 | 96.8 |
| EXAMPLE 11C | 370 | 90.1 | 3.2 | 1.6 | 96.6 |

In EXAMPLE 11C where the reactor is maintained at 370° C. a new peak in the GC chromatogram appears have an area-% of 3.6; thus, indicating a lower chemical yield of 1-hexene and formation of another product.

Example 12

Figure 7:
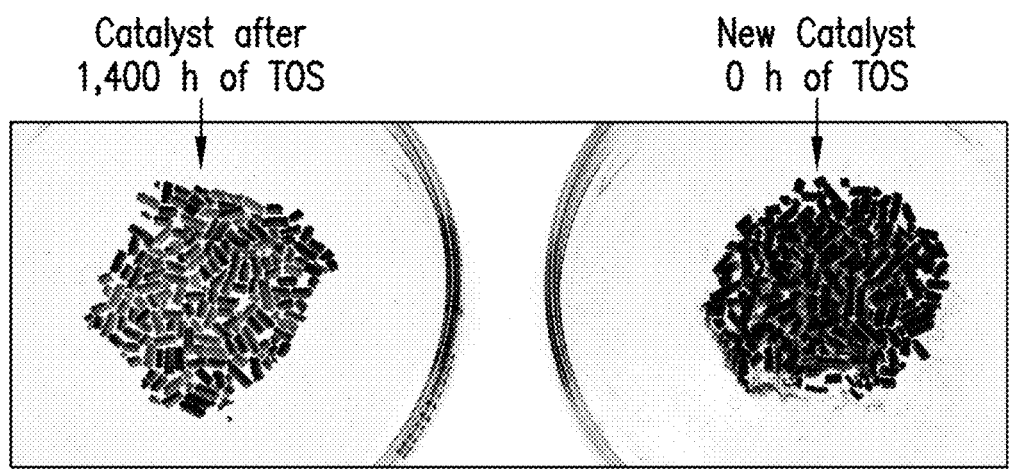
FIG. 7 is a photo comparing catalyst with 1400 h TOS (left) and new catalyst (on right).

After 1400 h of TOS for the dehydration of bio-1-octanol, some catalyst was removed at the entrance side of the tube reactor. In FIG. 7 the used catalyst is photographed next to catalyst with 0 h TOS. The used catalyst shows only a slight discoloration, and as noted herein, displays no loss in chemical conversion or loss in regioselectivity.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method for making a bio-alkene, comprising: dehydrating a bio-1-alcohol by heating the bio-1-alcohol in a reactor with a catalyst, wherein the resulting bio-alkene has a carbon chain of about 5 to about 20 carbon atoms and a bio-1-alkene regioselectivity of at least about 80%.

2. The method of claim 1, wherein the bio-alkene has a carbon chain of about 6 to about 14 carbon atoms.

3. The method according to claim 2, wherein the bio-alkene has a carbon chain length of about 6 to about 10 carbon atoms.

4. The method according to claim 3, wherein the bio-alkene has a carbon chain length of about 6 to about 8 carbon atoms.

5. The method according to claim 1, wherein the bio-alkene is bio-octene.

6. The method according to claim 1, wherein the reactor is a fixed bed reactor.

7. The method according to claim 6, wherein the fixed bed reactor is a fluidized bed reactor.

8. The method according to claim 1, wherein the catalyst is selected from $ZnAl_2O_4$ and a γ-alumina catalyst.

9. The method according to claim 1, wherein the bio-alkene has a bio-1-alkene regioselectivity of about 92% to about 99%.

10. The method according to claim 9, wherein the bio-alkene has a bio-1-alkene regioselectivity of about 95% to about 99%.

11. The method according to claim 1, wherein the catalyst is a γ-alumina catalyst is treated with a base to form a modified γ-alumina catalyst.

12. The method according to claim 11, wherein the base comprises a Group I or a Group II metal.

13. The method according to claim 11, wherein the γ-alumina catalyst is treated with a calcium promoter to provide a modified γ-alumina catalyst.

14. The method according to claim 13, wherein the modified γ-alumina catalyst is calcined to provide a calcined γ-alumina catalyst.

15. The method according to claim 13, wherein the calcium promoter is used in an amount of about 0.01 weight percent to about 4 weight percent based on the weight of CaO determined after calcination.

16. The method according to claim 15, wherein the calcium promoter is used in an amount of about 1 weight percent to about 2 weight percent based on the weight of CaO determined after calcination.

17. The method according to claim 14, wherein a temperature during calcination is about 400° C. to about 500° C.

18. The method according to claim 17, wherein the temperature during calcination is about 420° C. to about 480° C.

19. The method according to claim 18, wherein the temperature during calcination is about 440° C. to about 460° C.

20. The method according to claim 14, wherein calcination is carried out in an oven.

21. The method according to claim 14, wherein the calcination is carried out in an atmosphere of air or inert gas.

22. The method according to claim 1, wherein the method comprises a distillation step to refine the bio-alkene.

23. The method according to claim 1, wherein the bio-alkene results from a process wherein the bio-1-alcohol in water is dehydrated by heating the bio-1-alcohol with a catalyst under a purge gas.

24. The method according to claim 1, wherein the bio-alkene is further reacted to form a bio-based compound different from the bio-alkene or a bio-based polymer.

25. The method according to claim 24, wherein the bio-alkene is further reacted by a free radical or a catalytic polymerization process to form a bio-based polymer.

26. A bio-alkene made by the method of claim 1.

27. The bio-alkene according to claim 26, wherein the bio-alkene is selected from straight or branched chain bio-alkenes.

28. The bio-alkene according to claim 26, wherein the resulting bio-1-alkene is selected from bio-1-pentene, bio- 1-iso-pentene, bio-1-hexene, bio-1-heptene, bio-1-octene, bio-1-nonene, bio-1-decene, and bio-1-dodecene.

* * * * *

(12) INTER PARTES REVIEW CERTIFICATE (3856th)
United States Patent (10) Number: US 10,995,048 K1
Burgo et al. (45) Certificate Issued: Jan. 29, 2025

(54) NATURAL 1,2-ALKANEDIOLS, COMPOSITIONS HAVING NATURAL 1,2-ALKANEDIOLS AND PROCESSES FOR MAKING THE SAME

(71) Applicants: Rocco V. Burgo; Michael E. Wright; Gary B. Mosser; Michael J. Fevola

(72) Inventors: Rocco V. Burgo; Michael E. Wright; Gary B. Mosser; Michael J. Fevola

(73) Assignee: INOLEX INVESTMENT CORPORATION

Trial Number:

IPR2023-01035 filed Jun. 15, 2023

Inter Partes Review Certificate for:

Patent No.: 10,995,048
Issued: May 4, 2021
Appl. No.: 16/682,059
Filed: Nov. 13, 2019

The results of IPR2023-01035 are reflected in this inter partes review certificate under 35 U.S.C. 318(b).

INTER PARTES REVIEW CERTIFICATE
U.S. Patent 10,995,048 K1
Trial No. IPR2023-01035
Certificate Issued Jan. 29, 2025

AS A RESULT OF THE INTER PARTES REVIEW PROCEEDING, IT HAS BEEN DETERMINED THAT:

Claims 1-6, 8-10 and 22-28 are cancelled.

\* \* \* \* \*